US009788710B2

(12) United States Patent
Kuramoto

(10) Patent No.: US 9,788,710 B2
(45) Date of Patent: Oct. 17, 2017

(54) ENDOSCOPE SYSTEM AND LIGHT SOURCE DEVICE

(71) Applicant: FUJIFILM Corporation, Tokyo (JP)

(72) Inventor: Masayuki Kuramoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/402,870

(22) Filed: Jan. 10, 2017

(65) Prior Publication Data

US 2017/0127926 A1 May 11, 2017

Related U.S. Application Data

(62) Division of application No. 14/338,988, filed on Jul. 23, 2014, now Pat. No. 9,578,293.

(30) Foreign Application Priority Data

Sep. 27, 2013 (JP) ................. 2013-202553

(51) Int. Cl.
*A61B 1/06* (2006.01)
*G02B 23/24* (2006.01)
(Continued)

(52) U.S. Cl.
CPC ........ *A61B 1/0638* (2013.01); *A61B 1/00045* (2013.01); *A61B 1/04* (2013.01); *A61B 1/0684* (2013.01); *G02B 23/2469* (2013.01); *G02B 23/2484* (2013.01); *H04N 5/2256* (2013.01); *H04N 5/372* (2013.01); *H04N 5/378* (2013.01);
(Continued)

(58) Field of Classification Search
CPC ................................... A61B 1/0638
See application file for complete search history.

(56) References Cited

U.S. PATENT DOCUMENTS 8,531,512 B2 9/2013 Gono et al.
2007/0102623 A1* 5/2007 Fengler ............. A61B 1/00009
250/208.1
(Continued)

FOREIGN PATENT DOCUMENTS

JP 2006-218283 A 8/2006

OTHER PUBLICATIONS

Japanese Office Action dated Mar. 15, 2017 for JP Application No. 2016-089160.

*Primary Examiner* — Hung Dang
*Assistant Examiner* — Sunghyoun Park
(74) *Attorney, Agent, or Firm* — Birch, Stewart, Kolasch & Birch, LLP

(57) ABSTRACT

Violet narrowband light Vn and green narrowband light Gn produced by a light source device are supplied to a complementary color type endoscope, and simultaneously applied to an observation object. In a complementary color type imaging device, first mixed pixels and second mixed pixels, which sense both of the violet narrowband light Vn and the green narrowband light Gn, are read out. The light amount ratio Z of the violet narrowband light Vn to the green narrowband light Gn is set in such a range as to make the light amount of the violet narrowband light Vn larger than the light amount of the green narrowband light Gn, and make a signal value of the second mixed pixel higher than a signal value of the first mixed pixel.

6 Claims, 14 Drawing Sheets

(51) Int. Cl.
| | |
|---|---|
| *H04N 5/225* | (2006.01) |
| *H04N 9/04* | (2006.01) |
| *H04N 9/07* | (2006.01) |
| *H04N 5/372* | (2011.01) |
| *H04N 5/378* | (2011.01) |
| *H04N 9/12* | (2006.01) |
| *H04N 9/77* | (2006.01) |
| *H05B 33/08* | (2006.01) |
| *A61B 1/04* | (2006.01) |
| *A61B 1/00* | (2006.01) |

(52) U.S. Cl.
CPC ............... *H04N 9/045* (2013.01); *H04N 9/07* (2013.01); *H04N 9/12* (2013.01); *H04N 9/77* (2013.01); *H05B 33/0815* (2013.01); *H05B 33/0845* (2013.01); *H04N 2005/2255* (2013.01)

(56) References Cited

U.S. PATENT DOCUMENTS

| | | | |
|---|---|---|---|
| 2008/0174701 A1 | 7/2008 | Iketani | |
| 2009/0141125 A1 | 6/2009 | Yamazaki | |
| 2010/0266202 A1 | 10/2010 | Minai | |
| 2012/0271103 A1* | 10/2012 | Gono | A61B 1/00163 600/109 |
| 2013/0113908 A1* | 5/2013 | Watanabe | A61B 1/00009 348/70 |
| 2013/0148345 A1* | 6/2013 | Yabe | A61B 1/0638 362/231 |
| 2013/0286175 A1* | 10/2013 | Hashimoto | A61B 1/0638 348/68 |

* cited by examiner

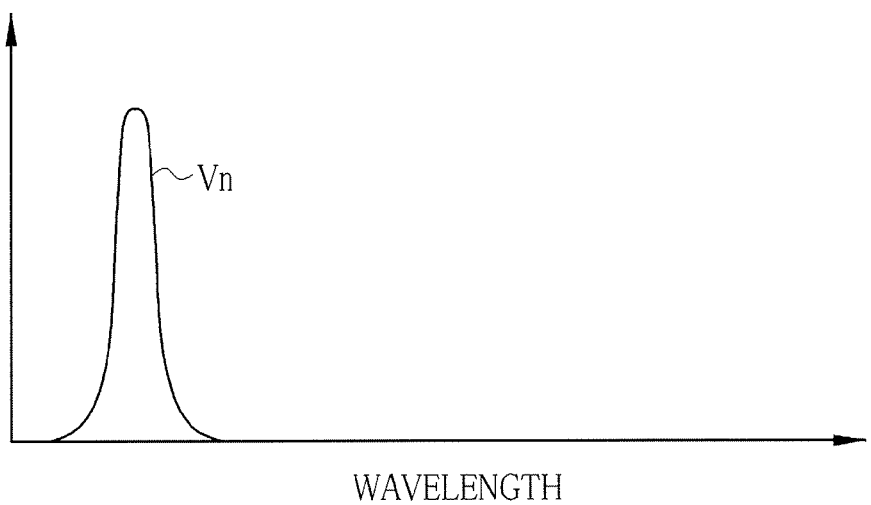
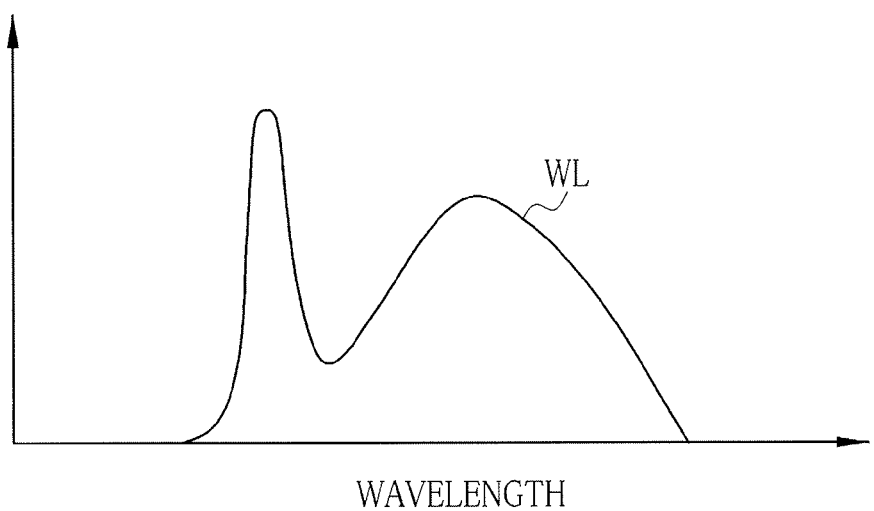

ENDOSCOPE SYSTEM AND LIGHT SOURCE DEVICE

CROSS-REFERENCE TO RELATED APPLICATIONS

This application is a Divisional of copending application Ser. No. 14/338,988, filed on Jul. 23, 2014, which claims priority under 35 U.S.C §119 to Japanese Patent Application No. 2013-202553 filed on Sep. 27, 2013. The above applications are hereby expressly incorporated by reference, in their entireties, into the present application.

BACKGROUND OF THE INVENTION

1. Field of the Invention

The present invention relates to an endoscope system for performing narrowband light observation using a complementary color type imaging device, and a light source device used in the endoscope system.

2. Description Related to the Prior Art

In a recent medical field, diagnosis and treatment using an endoscope system, having a light source device, an electronic endoscope, and a processor device, are widely performed. The light source device produces illumination light and applies the illumination light to the inside of a human body cavity. The electronic endoscope images the inside of the body cavity irradiated with the illumination light by an imaging device, and produces an imaging signal. The processor device applies image processing to the imaging signal produced by the electronic endoscope to produce an observation image to be displayed on a monitor.

As an observation method used in the endoscope system, there is known narrowband light observation using special light (narrowband light) having a narrow wavelength band as the illumination light, in addition to normal light observation using normal light (white light) having a wide wavelength band as the illumination light. The narrowband light observation, for example, can improve visibility of a blood vessel pattern in a superficial layer of a mucosa membrane, though the blood vessel pattern is easily buried in optical information obtained under irradiation with the white light. Therefore, the narrowband light observation allows focusing attention on superficial blood vessels of the blood vessel pattern, and diagnosing the stage of a disease, the depth of a lesion, and the like from the state of the superficial blood vessels.

The narrowband light observation uses two types of narrowband light absorbable by hemoglobin in blood, that is, blue narrowband light having a center wavelength in the vicinity of 415 nm and green narrowband light having a center wavelength in the vicinity of 540 nm. As an imaging method in the narrowband light observation, there are known a frame sequential method in which the blue narrowband light and the green narrowband light are alternately applied and a monochrome imaging device captures an image whenever each type of light is applied, and a simultaneous method in which the blue narrowband light and the green narrowband light are simultaneously applied and a simultaneous imaging device having color filters captures an image (see U.S. Pat. No. 8,531,512 and US Patent Application Publication No. 2009/0141125). The simultaneous method is inferior in resolution to the frame sequential method, but has the advantages of preventing a blur in the image and structural simplicity of the endoscope system.

The simultaneous imaging device includes a primary color type imaging device having primary color filters and a complementary color type imaging device having complementary color filters. The primary color type imaging device is used in an endoscope system that places importance on color, because of being superior in color reproducibility, though inferior in sensitivity, to the complementary color type imaging device. On the other hand, the complementary color type imaging device, which is superior in sensitivity and inferior in color reproducibility to the primary color type imaging device, is used in an endoscope system that places importance on sensitivity. Since the primary color type imaging device and the complementary color type imaging device have both advantage and disadvantage, it is desired that an endoscope system of the future be available with both of a primary color type endoscope containing the primary color type imaging device and a complementary color type endoscope containing the complementary color type imaging device.

The U.S. Pat. No. 8,531,512 and the US Patent Application Publication No. 2009/0141125 disclose a complementary color type imaging device of a complementary-color checkered-pattern color-difference line sequential method having four types of pixels of magenta (Mg), green (G), cyan (Cy), and yellow (Ye). According to the complementary-color checkered-pattern color-difference line sequential method, pixel signals are read out by a field readout method in a state of mixing (adding) the pixel signals of two adjoining rows. More specifically, the pixel signals are read out in a state of four types of combinations, i.e. the Mg pixel and the Cy pixel, the G pixel and the Ye pixel, the Mg pixel and the Ye pixel, and the G pixel and the Cy pixel. The complementary-color checkered-pattern color-difference line sequential method has the advantage of ease of producing a Y/C signal and an RGB signal just by addition and subtraction of the signals of the four types of mixed pixels.

In the case of performing the narrowband light observation by the endoscope system described above, according to the primary color type imaging device, blue (B) pixels capture the blue narrowband light and green (G) pixels capture the green narrowband light, independently. Thus, the primary color type imaging device can produce an image that has high color separability and high visibility of the superficial blood vessels (high contrast between the superficial blood vessels and the mucosa membrane). On the contrary, in the complementary color type imaging device, each mixed pixel senses the blue narrowband light and the green narrowband light at the same time (i.e. mixture of colors occurs). This causes low color separability, and a blur of the superficial blood vessels due to the influence of scattered light deteriorates the visibility of the superficial blood vessels.

In relation to this problem, the U.S. Pat. No. 8,531,512 and the US Patent Application Publication No. 2009/0141125 describe that changing coefficients of a matrix operation for converting a Y/C signal into an RGB signal in accordance with characteristics and the like of color filters reduces color mixture. However, this matrix operation is performed in a signal processing circuit that performs an operation of mixed pixel signals, and each of the mixed pixel signals is a signal in which a blue narrowband light component and a green narrowband light component have already been mixed at the time of entering the signal processing circuit. Therefore, the matrix operation cannot radically improve the color separability and the visibility of the superficial blood vessels.

SUMMARY OF THE INVENTION

An object of the present invention is to provide an endoscope system and a light source device that allow improvement in color separability and visibility of superficial blood vessels in narrowband light observation using a complementary color type imaging device.

To achieve the above and other objects, an endoscope system according to the present invention includes a complementary color type imaging device, a signal processing unit, and a lighting section. A first mixed pixel and a second mixed pixel, which sense both of first narrowband light and second narrowband light having a longer wavelength than the first narrowband light, are read out from the complementary color type imaging device. The signal processing unit images the first narrowband light by using a signal value of the first mixed pixel, and images the second narrowband light by using a signal value of the second mixed pixel. The lighting section has a light source device for simultaneously applying the first and second narrowband light to an observation object. In the light source device, the light amount ratio between the first narrowband light and the second narrowband light is set such that the light amount of the first narrowband light is made larger than the light amount of the second narrowband light and the signal value of the second mixed pixel is made higher than the signal value of the first mixed pixel.

The complementary color type imaging device preferably has a matrix of at least four types of pixels for performing photoelectric conversion of light of different colors. Two types of the four types of pixels next to in a vertical scan direction compose the first mixed pixel. Other two types of the four types of pixels next to in the vertical scan direction compose the second mixed pixel.

The light amount ratio is preferably set at a value "Z" satisfying the following expression (a):

$$1 < Z < Z_i \frac{S_2}{S_1} \quad (a)$$

wherein, $S_1$ represents the signal value of the first mixed pixel by independent application of only the first narrowband light, and $S_2$ represents the signal value of the second mixed pixel by independent application of only the second narrowband light, and $Z_i$ represents the light amount ratio of the first narrowband light to the second narrowband light in the independent application.

It is preferable that $S_1$ be an average of the signal values of a plurality of first mixed pixels by independent application of only the first narrowband light, and $S_2$ be an average of the signal values of a plurality of second mixed pixels by independent application of only the second narrowband light.

It is preferable that a complementary color type endoscope having the complementary color type imaging device and a primary color type endoscope having a primary color type imaging device be detachably connected to the light source device.

The endoscope system preferably includes a controller for controlling the light source device, such that the light amount ratio is set at a larger value in a case where the complementary color type endoscope is connected to the light source device than in a case where the primary color type endoscope is connected to the light source device.

The controller preferably sets the light amount ratio at "1" in a case where the primary color type endoscope is connected to the light source device, while the controller sets the light amount ratio at "Z" satisfying the expression (a) in a case where the complementary color type endoscope is connected to the light source device.

Each of the complementary color type endoscope and the primary color type endoscope preferably has information storage for storing specific information, and the controller preferably reads out the specific information from the information storage of the complementary color type endoscope or the primary color type endoscope that is connected to the light source device in order to judge the type of the connected endoscope.

The information storage of the complementary color type endoscope preferably stores an optimal light amount ratio satisfying the expression (a). In a case where the complementary color type endoscope is connected to the light source device, the controller determines the light amount ratio on the basis of the optimal light amount ratio read out of the information storage.

The endoscope system preferably has a calibration mode for calculating the optimal light amount ratio with applying the first and second narrowband light independently from the light source device. The controller preferably stores the optimal light amount ratio calculated in the calibration mode to the information storage of the complementary color type endoscope connected to the light source device.

The light source device preferably includes a plurality of LEDs. The controller preferably sets the light amount ratio by regulating at least one of light emission intensity and light emission time of the plurality of LEDs.

The endoscope system preferably includes a corrector for correcting a signal value M1 of the first mixed pixel and a signal value M2 of the second mixed pixel on the basis of the following expressions (b) and (c):

$$M1' = M1 - K_2 \times M2 \quad (b)$$

$$M2' = M2 - K_1 \times M1 \quad (c)$$

wherein, $K_1$ represents the ratio of the signal value of the second mixed pixel to the signal value of the first mixed pixel by independent application of only the first narrowband light, $K_2$ represents the ratio of the signal value of the first mixed pixel to the signal value of the second mixed pixel by independent application of only the second narrowband light.

Each of the four types of pixels preferably has one of color filter segments of cyan, magenta, yellow, and green arranged in a checkered pattern. The first mixed pixel is preferably a combination of a magenta pixel and a cyan pixel, and the second mixed pixel is preferably a combination of a green pixel and a yellow pixel. The first narrowband light preferably has a center wavelength in a blue or violet wavelength region, and the second narrowband light preferably has a center wavelength in a green wavelength region.

The endoscope system preferably includes a channel allocator for assigning the signal value of the first mixed pixel to a B channel and a G channel of an image display device, and assigning the signal value of the second mixed pixel to an R channel of the image display device, to display a special image.

The light amount ratio is preferably set at a value "Z" satisfying the following expression (d):

$$1 < Z < \frac{a_2}{a_1} \quad (d)$$

wherein, $a_1$ represents sensitivity of the first mixed pixel to the first narrowband light, and $a_2$ represents sensitivity of the second mixed pixel to the second narrowband light.

A light source device according to the present invention includes a light source and a light source controller for controlling the light source. The light source simultaneously produces first narrowband light and second narrowband light having a longer wavelength than the first narrowband light, and supplies the first and second narrowband light to an endoscope. A complementary color type imaging device from which a first mixed pixel and a second mixed pixel are read out is connectable to the light source device, and the first mixed pixel and the second mixed pixel sense both of the first narrowband light and the second narrowband light. The light source device simultaneously applies the first and second narrowband light to an observation object. The light source device sets the light amount ratio between the first narrowband light and the second narrowband light, such that the light amount of the first narrowband light is made larger than the light amount of the second narrowband light and the signal value of the second mixed pixel is made higher than the signal value of the first mixed pixel.

According to the present invention, the light amount ratio of the first narrowband light to the second narrowband light is determined such that the light amount of the first narrowband light is made larger than the light amount of the second narrowband light and the signal value of the second mixed pixel is made higher than the signal value of the first mixed pixel. Therefore, it is possible to improve the color separability and the visibility of the superficial blood vessels.

BRIEF DESCRIPTION OF DRAWINGS

For more complete understanding of the present invention, and the advantage thereof, reference is now made to the subsequent descriptions taken in conjunction with the accompanying drawings, in which:

FIG. 3 is a graph showing an emission spectrum of violet narrowband light;

FIG. 4 is a graph showing an emission spectrum of normal light;

DESCRIPTION OF THE PREFERRED EMBODIMENTS

Figure 1:
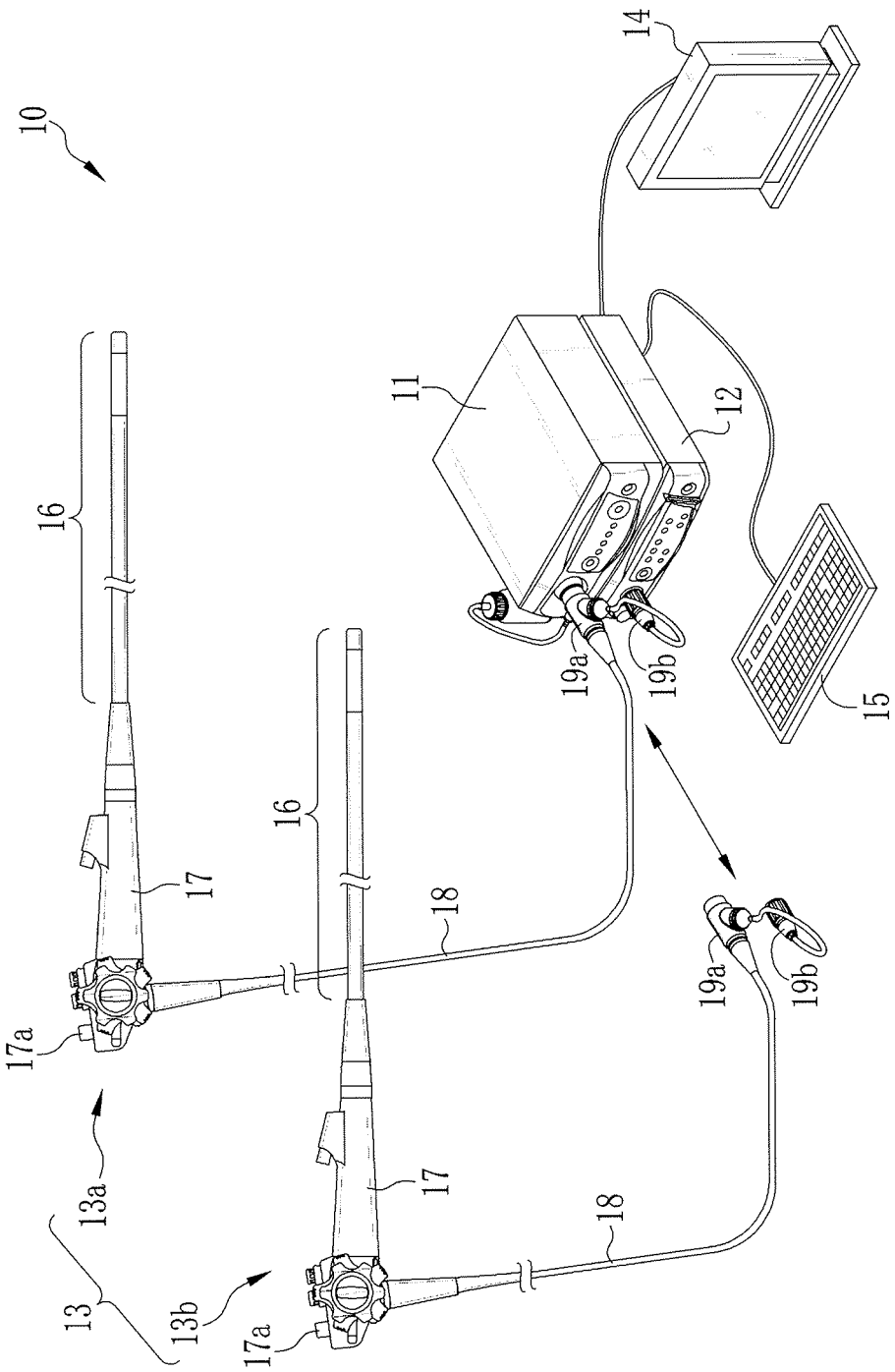
FIG. 1 is a schematic view of an endoscope system.

In FIG. 1, an endoscope system 10 is constituted of a light source device 11, a processor device 12, and electronic endoscopes 13 (hereinafter simply called endoscopes) detachably connected to the light source device 11 and the processor device 12. The light source device 11 produces illumination light and supplies the endoscope 13 with the illumination light. A distal end of the endoscope 13 is inserted into a human body cavity or the like to image the inside of the body cavity. The processor device 12 controls the imaging operation of the endoscope 13, and applies signal processing to an imaging signal obtained by the endoscope 13.

To the processor device 12, an image display device 14 and an input device 15 are connected. The image display device 14, being a liquid crystal display or the like, displays an image of an observation object inside the body cavity produced by the processor device 12. The input device 15, including a keyboard and a mouse, is used for inputting various types of information to the processor device 12.

Figure 2:
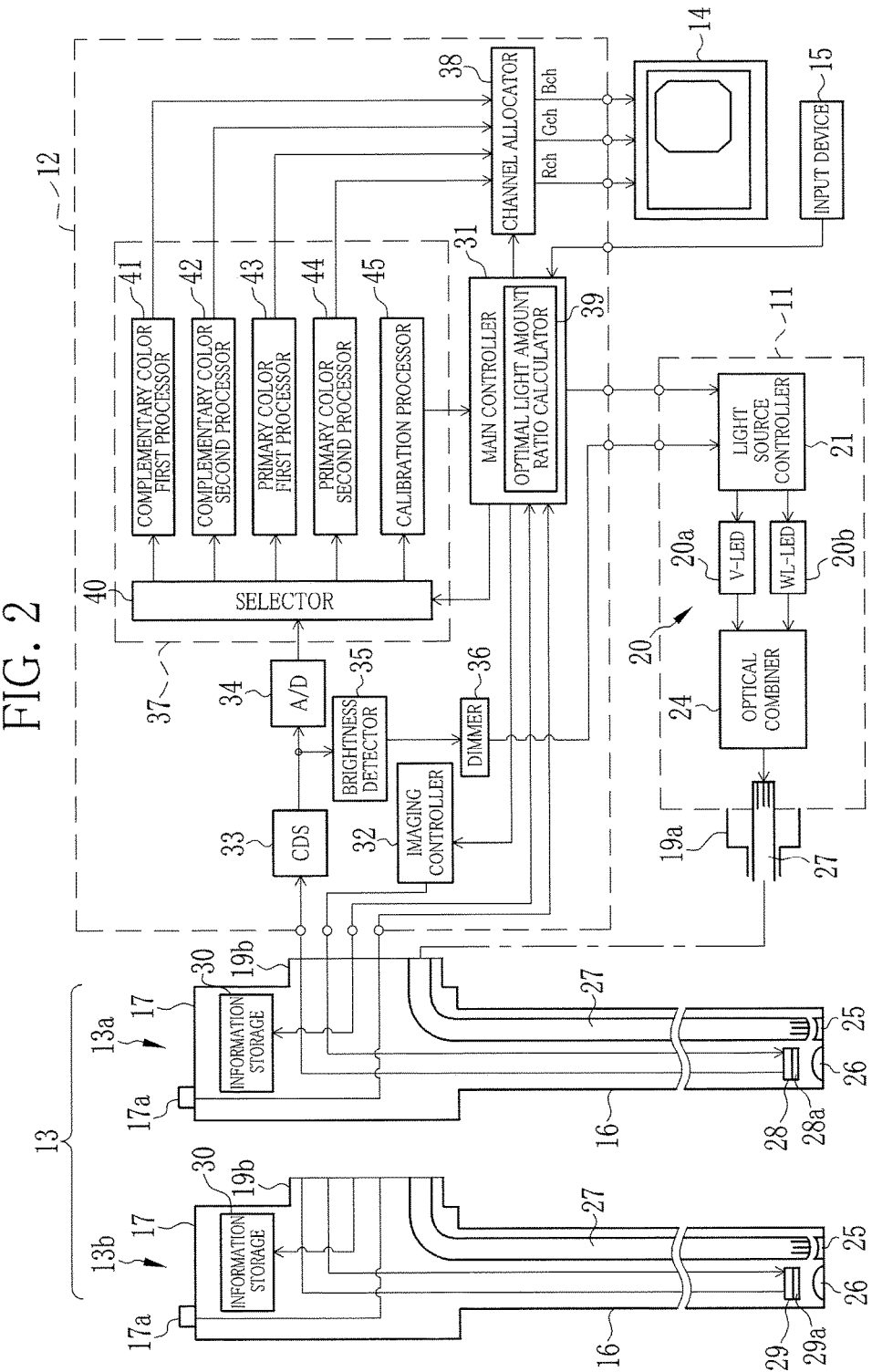
FIG. 2 is a block diagram of the endoscope system.

The endoscopes 13 include a complementary color type endoscope 13*a* having a complementary color type imaging device 28 (see FIG. 2) and a primary color type endoscope 13*b* having a primary color type imaging device 29 (see FIG. 2). Either of the complementary color type endoscope 13*a* and the primary color type endoscope 13*b* is connectable to the light source device 11 and the processor device 12. The complementary color type endoscope 13*a* and the primary color type endoscope 13*b* have identical structure except for the imaging device. Each endoscope 13*a* or 13*b* includes an insert section 16, a control handle unit 17, a universal cable 18, a light guide connector 19*a*, and a signal connector 19*b*.

The slender insert section 16 is introduced into the human body cavity or the like. The control handle unit 17 is coupled to a rear end of the insert section 16. The control handle unit 17 is provided with various switches, a bending operation dial, and the like. The various switches include a mode switch 17*a* for switching an operation mode.

The universal cable 18 extends from the control handle unit 17. The light guide connector 19*a* and the signal connector 19*b* are attached to an end of the universal cable 18. The light guide connector 19*a* is detachably connected to the light source device 11. The signal connector 19*b* is detachably connected to the processor device 12.

As an observation mode of the endoscope system 10, there are provided a normal light observation mode and a narrowband light observation mode. In the normal light observation mode, the observation object is imaged under irradiation with normal light (white light) having a wavelength band extending from the blue region to the red region, and a normal image is produced. In the narrowband light observation mode, the observation object is imaged under irradiation with narrowband light (violet narrowband light Vn and green narrowband light Gn, described later on) having a narrow wavelength band, and a narrowband light image is produced. Both of the complementary color type endoscope 13a and the primary color type endoscope 13b can carry out the normal light observation mode and the narrowband light observation mode.

The endoscope system 10 is switchable between the normal light observation mode and the narrowband light observation mode by operation of the mode switch 17a described above, but may be switched by operation of a foot switch (not shown) connected to the processor device 12, a button provided on a front panel of the processor device 12, the input device 15, or the like.

In FIG. 2, the light source device 11 has an LED (light emitting diode) light source 20, a light source controller 21, and an optical combiner 24. The LED light source 20 includes a violet LED (V-LED) 20a and a white LED (WL-LED) 20b. Referring to FIG. 3, the V-LED 20a produces violet narrowband light Vn having a wavelength band of 380 to 440 nm. Referring to FIG. 4, the WL-LED 20b produces white light WL of a wide wavelength band. The light source controller 21 controls light emission from the V-LED 20a and the WL-LED 20b.

Figure 5:
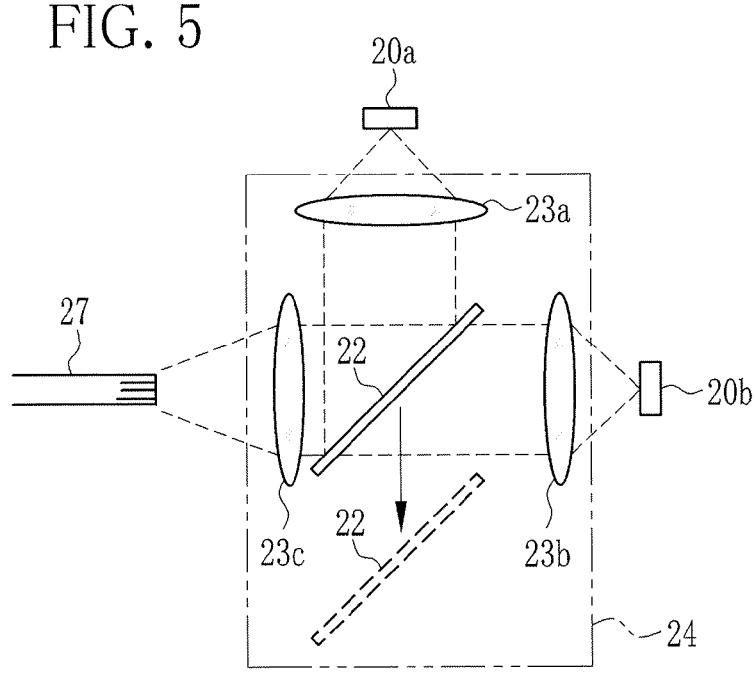
FIG. 5 is an explanatory view of the structure of an optical combiner.

As shown in FIG. 5, the optical combiner 24 has a dichroic mirror 22 and first to third lenses 23a to 23c. The first lens 23a is disposed in front of the LED 20a, and gathers and collimates the light emitted from the LED 20a. The second lens 23b is disposed in front of the LED 20b, and gathers and collimates the light emitted from the LED 20b. The V-LED 20a and the WL-LED 20b are disposed such that optical axes of the V-LED 20a and the WL-LED 20b are orthogonal to each other. The dichroic mirror 22 is situated at an intersection point of the optical axes.

Figure 6:
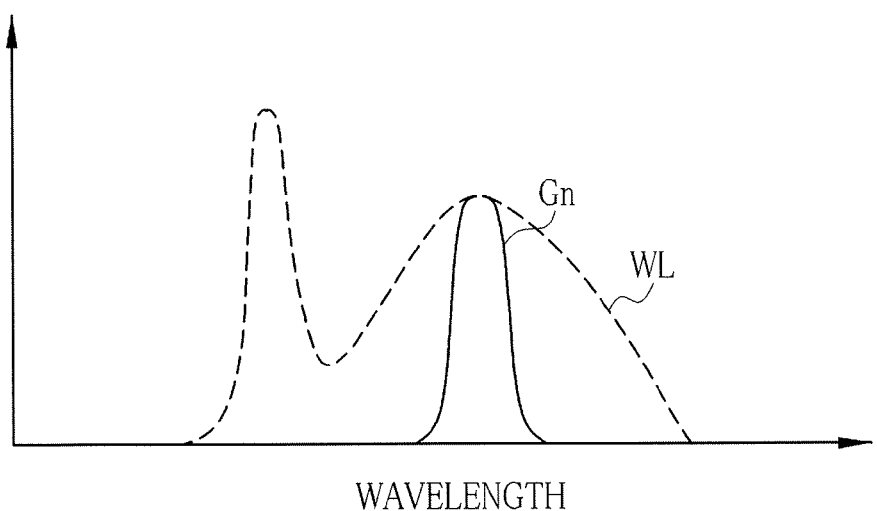
FIG. 6 is a graph showing an emission spectrum of green narrowband light.

The dichroic mirror 22 transmits light in a wavelength band of 530 nm or more and less than 550 nm, and reflects light in a wavelength of less than 530 nm or 550 nm or more, for example. Thus, the violet narrowband light Vn is reflected by the dichroic mirror 22 and gathered by the third lens 23c. On the other hand, a part of the white light WL is passed through the dichroic mirror 22, and gathered by the third lens 23c as green narrowband light Gn having a wavelength band of 530 to 550 nm, as shown in FIG. 6.

In the narrowband light observation mode, the V-LED 20a and the WL-LED 20b are simultaneously turned on. The violet narrowband light Vn and the green narrowband light Gn are combined (mixed) by the dichroic mirror 22 and gathered by the third lens 23c, and enter a light guide 27.

In the normal light observation mode, a shift mechanism (not shown) moves the dichroic mirror 22 out of the optical axis of the WL-LED 20b. Thus, in the normal light observation mode, the white light WL is directly incident upon the third lens 23c, and led into the light guide 27. Since the dichroic mirror 22 is retracted in the normal light observation mode, the violet narrowband light Vn emitted from the V-LED 20a is not incident upon the third lens 23c even if the dichroic mirror 22 reflects the violet narrowband light Vn. Thus, the V-LED 20a is preferably turned off, but there is no harm in turning on the V-LED 20a.

The center wavelength of the violet narrowband light Vn is approximately 405 nm at which hemoglobin has a high absorption coefficient in the visible region. The center wavelength of the green narrowband light Gn is approximately 540 nm at which hemoglobin has a high absorption coefficient in the green wavelength region. The green narrowband light Gn has a higher reflectance from a mucosa membrane than the violet narrowband light Vn.

The insert section 16 of the endoscope 13 has at its tip end a lighting window and an image capturing window provided next to each other. A lighting lens 25 is fitted into the lighting window. An objective lens 26 is fitted into the image capturing window. The light guide 27 extends through the endoscope 13, and one end of the light guide 27 is opposed to the lighting lens 25. The other end of the light guide 27 is provided with the light guide connector 19a. In a state of fitting the light guide connector 19a to the light source device 11, the other end of the light guide 27 is inserted into the light source device 11.

The lighting lens 25 gathers the light that is transmitted from the light source device 11 through the light guide 27 and ejected from the light guide 27, and applies the light to the observation object inside the body cavity. The objective lens 26 gathers reflected light from living body tissue and the like of the observation object, and forms an optical image. In an image forming position of the objective lens 26, an imaging device (the complementary color type imaging device 28 in the case of the complementary color type endoscope 13a, the primary color type imaging device 29 in the case of the primary color type endoscope 13b) is disposed to capture the optical image and produce the imaging signal. The complementary color type imaging device 28 and the primary color type imaging device 29 are CCD (charge coupled device) image sensors.

Figure 7:
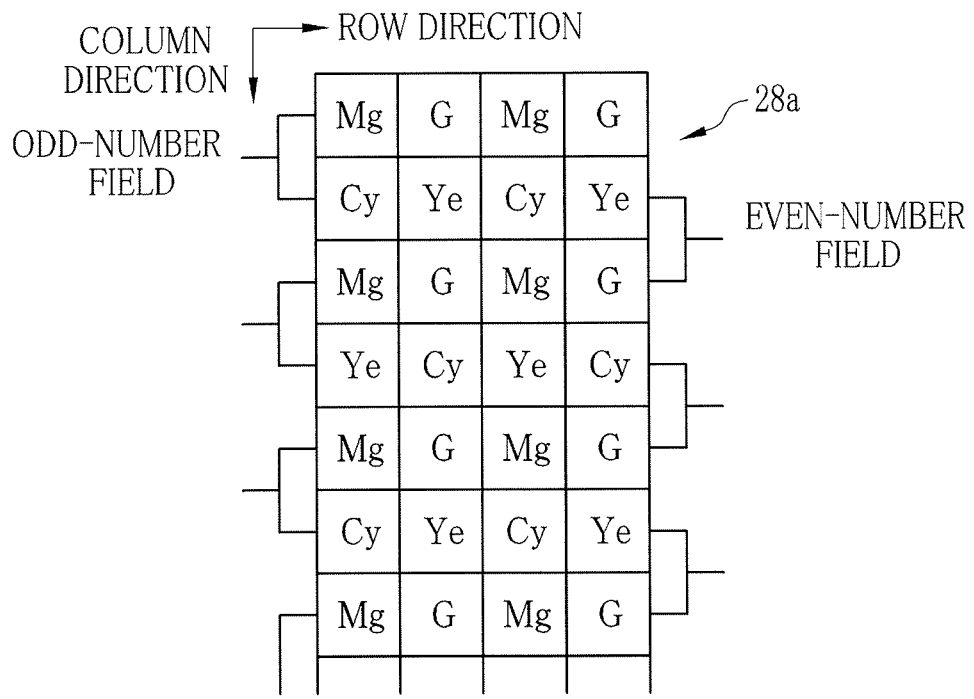
FIG. 7 is a schematic view of a complementary color type color separation filter.

The complementary color type imaging device 28 is provided at its imaging surface with a complementary color type color separation filter 28a to perform optical color separation of the optical image on a pixel-by-pixel basis. As shown in FIG. 7, this complementary color type color separation filter 28a has four types of color filter segments of magenta (Mg), green (G), cyan (Cy), and yellow (Ye), and one color filter segment is provided for each pixel. Accordingly, the complementary color type imaging device 28 has four types of pixels of Mg, G, Cy, and Ye. The Mg pixels and the G pixels are alternately arranged in odd-number rows, and the Cy pixels and the Ye pixels are alternately arranged in even-number rows, such that the Mg pixel, the Cy pixel, the Mg pixel, the Ye pixel, . . . are arranged in this order in odd-number columns, and the G pixel, the Ye pixel, the G pixel, the Cy pixel . . . are arranged in this order in even-number columns. This color filter pattern is referred to as a complementary-color checkered-pattern color-difference line sequential method. A row direction refers to a horizontal scan direction, and a column direction refers to a vertical scan direction.

Figure 8:
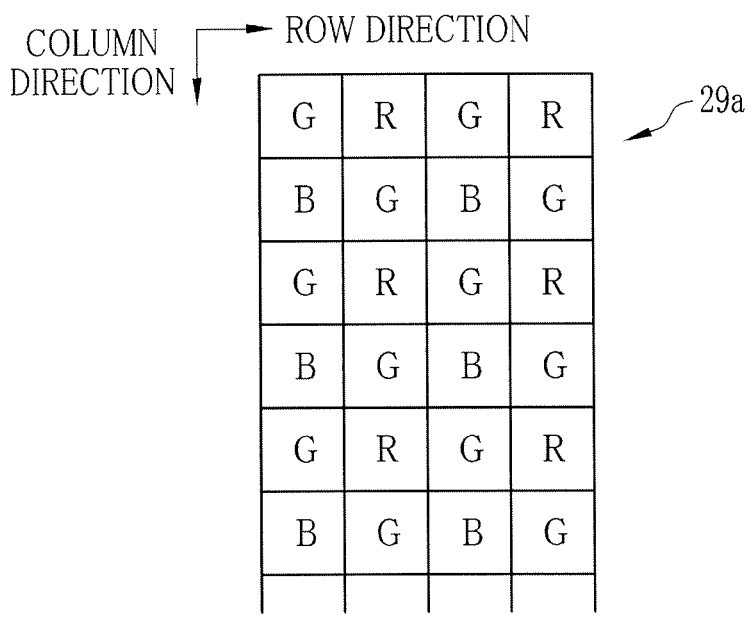
FIG. 8 is a schematic view of a primary color type color separation filter.

The primary color type imaging device 29 is provided at its imaging surface with a primary color type color separation filter 29a. As shown in FIG. 8, this primary color type color separation filter 29a has three types of color filter segments of red (R), green (G), and blue (B), which are three primary colors of an additive color process. One color filter segment is provided for each pixel. Accordingly, the primary color type imaging device 29 has three types of pixels of R, G, and B. The G pixels and the B pixels are alternately arranged in odd-number columns, and the R pixels and the G pixels are alternately arranged in even-number columns. The G pixels and the R pixels are alternately arranged in odd-number rows, and the B pixels and the G pixels are alternately arranged in even-number rows. This color filter pattern is referred to as a primary color Bayer pattern.

The endoscope 13 includes information storage 30 composed of a non-volatile memory such as a flash memory. The information storage 30 stores specific information (the color filter pattern and the pixel number of the imaging device) and the like of the endoscope 13.

The processor device 12 has a main controller 31, an imaging controller 32, a correlated double sampling (CDS) circuit 33, an A/D converter 34, a brightness detector 35, a dimmer 36, a signal processing unit 37, and a channel allocator 38.

The main controller 31 controls each part of the processor device 12 and the light source device 11. Upon connecting the endoscope 13 to the light source device 11 and the processor device 12, the main controller 31 reads the specific information of the endoscope 13 from the information storage 30, and judges whether the connected endoscope 13 is the complementary color type endoscope 13a or the primary color type endoscope 13b. The imaging controller 32 actuates the imaging device (complementary color type imaging device 28 or the primary color type imaging device 29) in accordance with the type of the endoscope 13 judged by the main controller 31.

Figure 9:
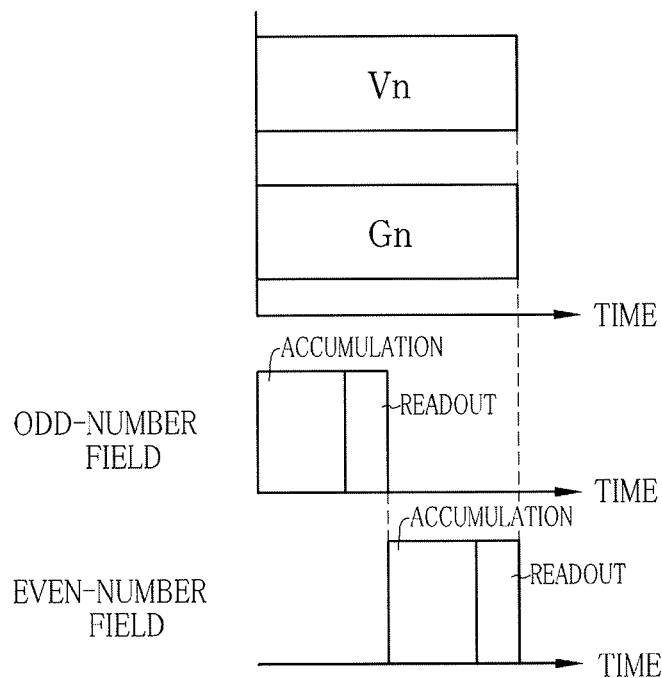
FIG. 9 is a timing chart of light sources and a complementary color type imaging device in a narrowband light observation mode.

In the case of the complementary color type imaging device 28, the imaging controller 32 drives the complementary color type imaging device 28 by a field readout method in synchronization with emission timing of the light source device 11. To be more specific, according to the field readout method, pixel signals of two pixels adjoining in the column direction (vertical scan direction) are read out in a mixed (added) manner in reading each of an odd-number field and an even-number field (see FIG. 7). The mixture of the pixel signals is performed in a horizontal transfer path (not shown) of the CCD image sensor by using the pixel signals of two rows. FIG. 9 shows a timing chart of the narrowband light observation mode. A timing chart of the normal light observation mode is the same as that of the narrowband light observation mode, except that the illumination light is the white light WL.

Figure 10:
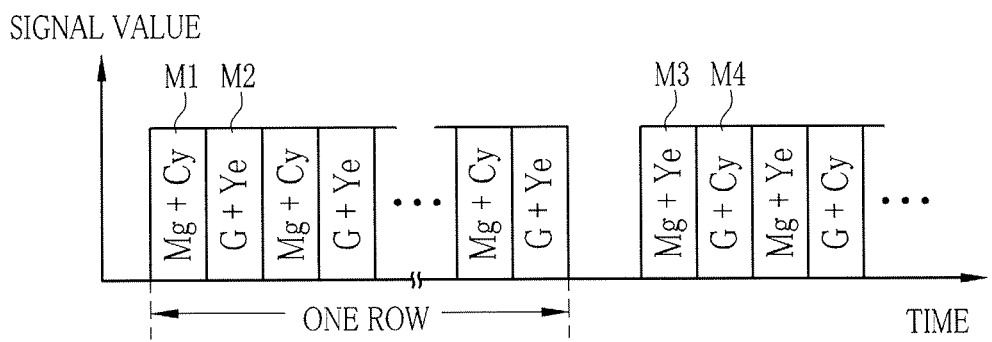
FIG. 10 is an explanatory view of output signals from the complementary color type imaging device.

According to the field readout method, as shown in FIG. 10, a mixed pixel signal (hereinafter called a first mixed pixel signal) M1 of the Mg pixel and the Cy pixel, a mixed pixel signal (hereinafter called a second mixed pixel signal) M2 of the G pixel and the Ye pixel, a mixed pixel signal (hereinafter called a third mixed pixel signal) M3 of the Mg pixel and the Ye pixel, and a mixed pixel signal (hereinafter called a fourth mixed pixel signal) M4 of the G pixel and the Cy pixel are read out from the complementary color type imaging device 28 in each of the odd-number field and the even-number field.

Figure 11:
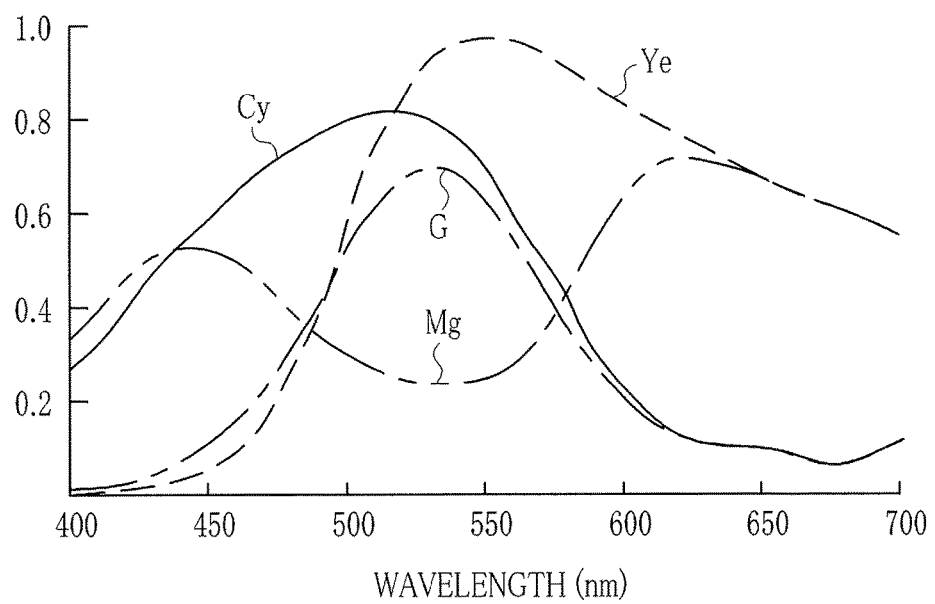
FIG. 11 is a graph of spectral sensitivity characteristics of the complementary color type imaging device.
Figure 12:
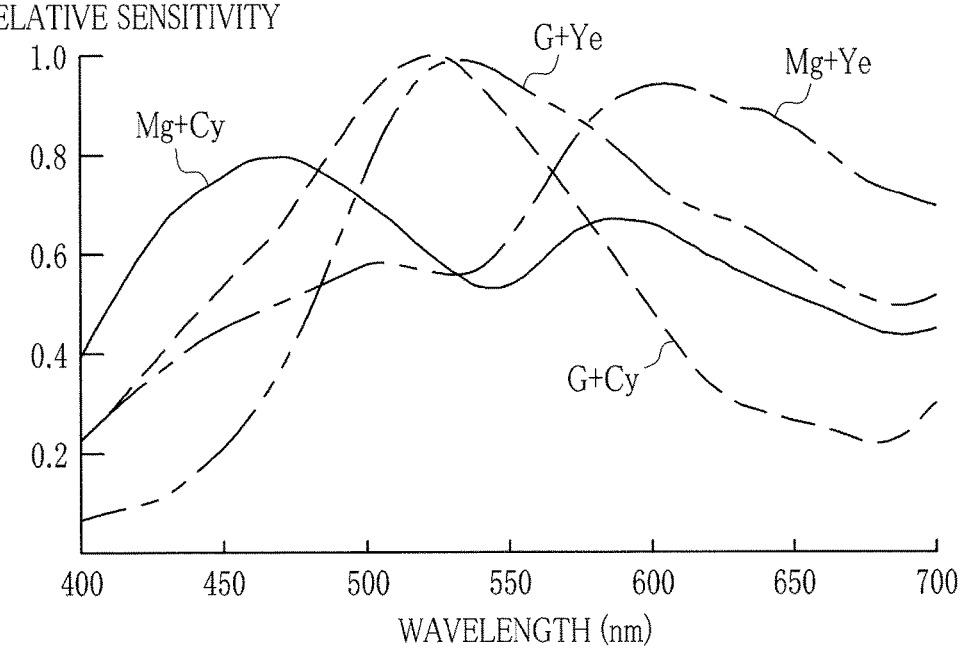
FIG. 12 is a graph of spectral sensitivity characteristics of first to fourth mixed pixels.

Since the pixels of the complementary color type imaging device 28 have spectral sensitivity characteristics as shown in FIG. 11, for example, in accordance with the color filter segments provided thereto, the mixed pixels have spectral sensitivity characteristics as shown in FIG. 12, for example. As is apparent from the spectral sensitivity characteristics, out of the first to fourth mixed pixels, the first mixed pixel (Mg+Cy) is the most sensitive to the violet narrowband light Vn (a center wavelength of 405 nm), and the second mixed pixel (G+Ye) is the most sensitive to the green narrowband light Gn (a center wavelength of 540 nm). However, the first mixed pixel (Mg+Cy) has high sensitivity to the green narrowband light Gn too. The second mixed pixel (G+Ye) has a little sensitivity to the violet narrowband light Vn.

In the narrowband light observation mode, the violet narrowband light Vn is imaged based on the first mixed pixel signal M1, and the green narrowband light Gn is imaged based on the second mixed pixel signal M2. On the other hand, in the normal light observation mode, imaging is performed by using all of the first to fourth mixed pixel signals M1 to M4.

In the case of the primary color type imaging device 29, the imaging controller 32 drives the primary color type imaging device 29 by a well-known progressive readout method in synchronization with emission timing of the light source device 11. According to the progressive readout method, the pixel signals of one frame are read out sequentially and individually on a row-by-row basis, without mixing the pixel signals.

A signal outputted from the complementary color type imaging device 28 or the primary color type imaging device 29 is inputted to the CDS circuit 33. The CDS circuit 33 applies correlated double sampling to the inputted signal to remove a noise component occurring in the CCD image sensor. The signal, after the noise removal by the CDS circuit 33, is inputted to the A/D converter 34 and the brightness detector 35. The A/D converter 34 converts the signal inputted from the CDS circuit 33 into a digital signal, and inputs the digital signal to the signal processing unit 37.

The brightness detector 35 detects as brightness (average luminance of the signal) an average value of G signals, in general, based on the signal inputted from the CDS circuit 33. The dimmer 36 produces a dimming signal, which represents the difference between a brightness signal detected by the brightness detector 35 and standard brightness (a target dimming value). This dimming signal is inputted to the light source controller 21. The light source controller 21 adjusts the light emission amount of the LED light source 20 so as to obtain the standard brightness.

Upon receiving a mode switching signal issued by the operation of the mode switch 17a of the endoscope 13, the main controller 31 switches a light emission method of the light source device 11 and a signal processing method of the signal processing unit 37 in accordance with the received mode switching signal.

In the narrowband light observation mode, the main controller 31 controls the light source controller 21 in accordance with the type of the endoscope 13 defined by the specific information read out of the information storage 30 so as to change the light emission intensity of the V-LED 20a and the WL-LED 20b. More specifically, in the case of the primary color type endoscope 13b, the main controller 31 controls the light source controller 21 so as to substantially equalize the light amounts of the violet narrowband light Vn and the green narrowband light Gn applied from the primary color type endoscope 13b to the observation object.

On the other hand, in the case of the complementary color type endoscope 13a, the main controller 31 controls the light source controller 21 such that the light amount ratio Z of the light amount X of the violet narrowband light Vn to the light amount Y of the green narrowband light Gn applied from the complementary color type endoscope 13a to the observation object satisfies the following expression (1). This light amount ratio Z (Z=X/Y) is at least larger than the light amount ratio (Z=1) in the case of the primary color type endoscope 13b.

$$1 < Z < Z_i \frac{S_2}{S_1} \tag{1}$$

wherein, $S_1$ represents a first mixed pixel signal M1v obtained in the case of independently applying only the violet narrowband light Vn. $S_2$ represents a second mixed pixel signal M2g obtained in the case of independently applying only the green narrowband light Gn. $Z_i$ represents the ratio $(X_i/Y_i)$ of the light amount $X_i$ of the violet narrowband light Vn to the light amount $Y_i$ of the green narrowband light Gn in the independent application.

The expression (1) corresponds to a condition of the light amount ratio Z for making the light amount X of the violet narrowband light Vn higher than the light amount Y of the green narrowband light Gn that are simultaneously applied to the observation object, and for making a signal value of the second mixed pixels used for imaging the green narrowband light Gn higher than a signal value of the first mixed pixels used for imaging the violet narrowband light Vn. Therefore, it is possible to improve color separability and the visibility of superficial blood vessels (the contrast between the superficial blood vessels and the mucosa membrane), as described later on.

Especially, the light amount ratio Z is preferably set at an optimal light amount ratio $Z_0$ represented by the following expression (2). This optimal light amount ratio $Z_0$ is a median value of the confines defined by the expression (1).

$$Z_0 = \frac{1}{2}\left(Z_i \frac{S_2}{S_1} + 1\right) \qquad (2)$$

It is preferable that $S_1$ be an average value of a plurality of first mixed pixel signals M1v in independent application of the violet narrowband light Vn, (for example, an average value of all the first mixed pixel signals M1v in the odd-number field and the even-number field). Likewise, it is preferable that $S_2$ be an average value of a plurality of second mixed pixel signals M2g in independent application of the green narrowband light Gn, (for example, an average value of all the second mixed pixel signals M2g in the odd-number field and the even-number field).

To obtain this optimal light amount ratio $Z_0$, in a final test process or the like in the course of manufacturing the endoscope system 10, the violet narrowband light Vn and the green narrowband light Gn are independently emitted (by time-sharing emission) from the light source device 11 at a predetermined light amount ratio $Z_i$ (for example, $Z_i$=1), and the first and second mixed pixel signals M1v and M2g are obtained by the complementary color type imaging device 28, and the optimal light amount ratio $Z_0$ is calculated from the expression (2). The optimal light amount ratio $Z_0$ obtained in the course of manufacturing is recorded to the image storage 30 of the complementary color type endoscope 13a.

Provided that the complementary color type endoscope 13a is connected to the light source device 11 and the processor device 12 and the narrowband light observation mode is chosen by operation of the mode switch 17a, the main controller 31 reads out the optimal light amount ratio $Z_0$ stored in the information storage 30 of the complementary color type endoscope 13a. The main controller 31 controls the light source controller 21 to set the light emission intensity of the V-LED 20a and the WL-LED 20b by intensity modulation, such that the complementary color type endoscope 13a emits the violet narrowband light Vn and the green narrowband light Gn at the light amount ratio Z satisfying the expression (1).

Figure 13:
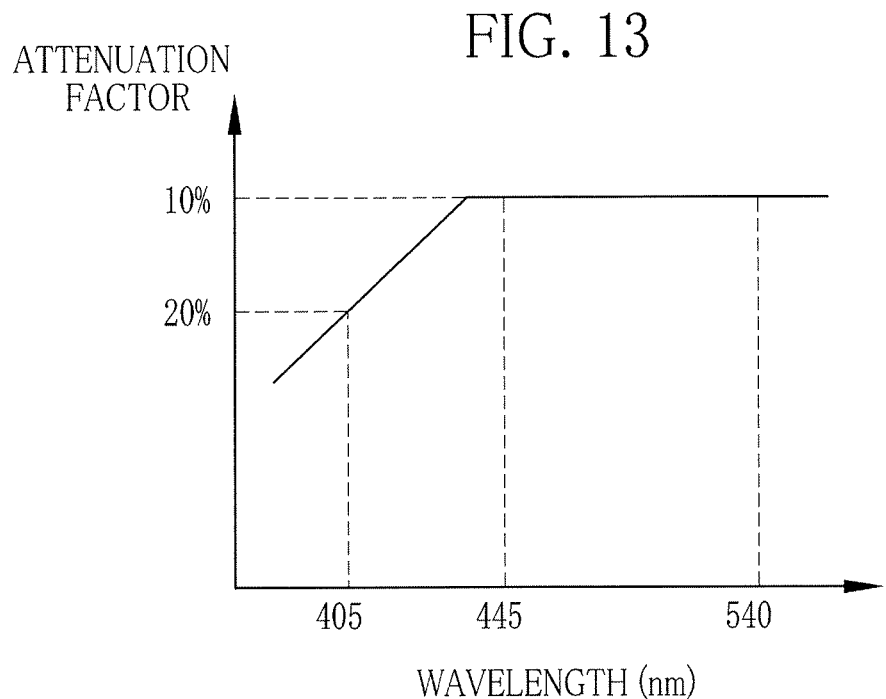
FIG. 13 is a graph of a spectral attenuation characteristic of a light guide.

The above light guide 27 has a spectral attenuation characteristic as shown in FIG. 13. An attenuation factor of propagating light is increased in a short wavelength range of approximately 440 nm or less. Thus, the violet narrowband light Vn emitted from the light source device 11 attenuates more strongly than the green narrowband light Gn in the light guide 27 of the complementary color type endoscope 13a. As a result, since the light emission intensity ratio between the V-LED 20a and the WL-LED 20b does not coincide with the light amount ratio Z between the violet narrowband light Vn and the green narrowband light Gn emitted from the complimentary color type endoscope 13a, the main controller 31 determines the light emission intensity of the V-LED 20a and the WL-LED 20b in consideration of the spectral attenuation factor of the light guide 27. For example, the relation between the light emission intensity ratio of the V-LED 20a and the WL-LED 20b and the light amount ratio Z of the violet narrowband light Vn and the green narrowband light Gn emitted from the complementary color type endoscope 13a is measured in advance and put into a table. The V-LED 20a and the WL-LED 20b may be controlled based on this table.

Figure 14:
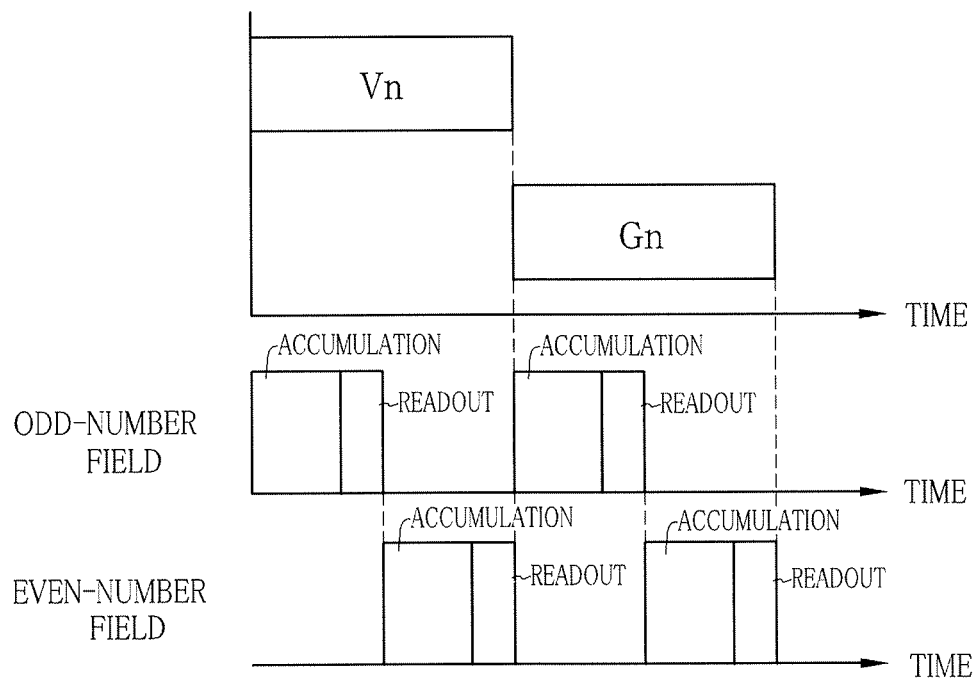
FIG. 14 is a timing chart of the light sources and the complementary color type imaging device in a calibration mode.

The endoscope system 10 has a calibration mode for allowing recalculation of the optimal light amount ratio $Z_0$ after the completion of the manufacture as a product. The calibration mode is chosen by operation of the input device 15 or the like. In the calibration mode, the main controller 31 turns on the V-LED 20a and the WL-LED 20b independently. Thus, as shown in FIG. 14, the violet narrowband light Vn and the green narrowband light Gn are applied in a time sharing manner, and the complementary color type imaging device 28 is driven in synchronization with emission timing.

In the calibration mode, the light amount ratio Z set in the light source controller 21 is used as the light amount ratio $Z_i$ between the violet narrowband light Vn and the green narrowband light Gn. The main controller 31 includes an optimal light amount ratio calculator 39. The optimal light amount ratio calculator 39 calculates the optimal light amount ratio $Z_0$ by the expression (2).

The signal processing unit 37 includes a selector 40, a complementary color first processor 41, a complementary color second processor 42, a primary color first processor 43, a primary color second processor 44, and a calibration processor 45. The selector 40 chooses one of the processors 41 to 45 in accordance with the type and the operation mode of the endoscope 13 judged by the main controller 31.

The calibration processor 45 is chosen in the above calibration mode. In the calibration mode, a signal outputted from the complementary color type imaging device 28 is inputted to the signal processing unit 37 through the CDS circuit 33 and the A/D converter 34, and sent to the calibration processor 45 via the selector 40. The calibration processor 45 extracts the above first and second mixed pixel signals M1v and M2g from the input signal. The calibration processor 45 calculates an average of signal values of each of the first and second mixed pixel signals M1v and M2g, and inputs the averages to the optimal light amount ratio calculator 39 of the main controller 31. The optimal light amount ratio calculator 39 calculates the optimal light amount ratio $Z_0$ from the expression (2) with the use of the signal values inputted from the calibration processor 45.

After performing the calibration, the main controller 31 deletes the optimal light amount ratio $Z_0$ that has been stored in the information storage 30 of the complementary color type endoscope 13a, and replaces it with the optimal light amount ratio $Z_0$ that is newly calculated by the optimal light amount ratio calculator 39.

The complementary color first processor 41 is chosen in a case where the endoscope 13 is of the complementary color type and the observation mode is the normal light observation mode. To the complementary color first processor 41, the first to fourth mixed pixel signals M1 to M4 (see FIG. 10) are inputted from the complementary color type imaging device 28. The complementary color first processor 41 produces a luminance signal Y and color difference signals Cr and Cb by performing a well-known Y/C conversion used in the complementary-color checkered-pattern color-difference line sequential method, and then converts the luminance signal Y and the color difference signals Cr and Cb into the RGB signal by a matrix operation. This RGB signal is sent to the channel allocator 38. More specifically, the luminance signal Y and the color difference signals Cr and Cb are calculated by addition and subtraction of the first mixed pixel signal M1 and the second mixed pixel signal M2 next to each other in the row direction and addition and subtraction of the third mixed pixel signal M3 and the fourth mixed pixel signal M4 next to each other in the row direction.

Figure 15:
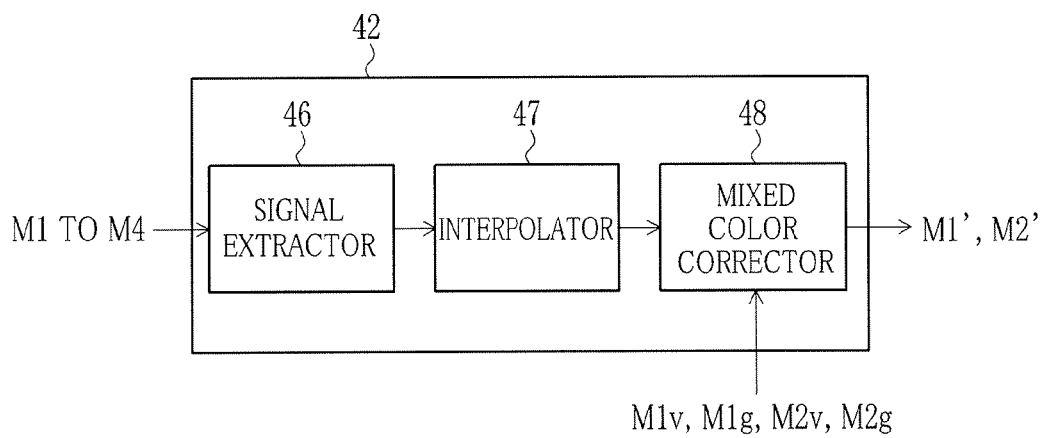
FIG. 15 is a block diagram of a complementary color first processor.

The complementary color second processor 42 is chosen in a case where the endoscope 13 is of the complementary color type and the observation mode is the narrowband light observation mode. As shown in FIG. 15, the complementary color second processor 42 has a signal extractor 46, an interpolator 47, and a mixed color corrector 48.

The signal extractor 46 extracts only the first and second mixed pixel signals M1 and M2 out of the first to fourth mixed pixel signals M1 to M4 inputted from the complementary color type imaging device 28, and inputs the first and second mixed pixel signals M1 and M2 to the interpolator 47. The interpolator 47 performs a well-known pixel interpolation processing, to produce two signals of the first and second mixed pixel signals M1 and M2 in the position of each mixed pixel. The mixed color corrector 48 performs mixed color correction processing by using the following expression (3):

$$\begin{pmatrix} M1' \\ M2' \end{pmatrix} = \begin{pmatrix} 1 & -K_2 \\ -K_1 & 1 \end{pmatrix} \begin{pmatrix} M1 \\ M2 \end{pmatrix} \quad (3)$$

wherein, $K_1$ represents the ratio ($M2v/M1v$) of a second mixed pixel signal $M2v$ to a first mixed pixel signal $M1v$ obtained in independent application of only the violet narrowband light Vn. $K_2$ represents the ratio ($M1g/M2g$) of a first mixed pixel signal $M1g$ to a second mixed pixel signal $M2g$ obtained in independent application of only the green narrowband light Gn.

The mixed color corrector 48 calculates correction coefficients $K_1$ and $K_2$ with the use of the first mixed pixel signals $M1v$ and $M1g$ and the second mixed pixel signals $M2g$ and $M2v$ obtained in the above calibration mode. The mixed color corrector 48 keeps holding the calculated correction coefficients $K_1$ and $K_2$ until the calibration is performed again.

The correction coefficients $K_1$ and $K_2$ may be obtained in the course of manufacture and stored to the information storage 30 of the complementary color type endoscope 13a, and the main controller 31 may obtain the correction coefficients $K_1$ and $K_2$ from the information storage 30 at the time when the complementary color type endoscope 13a is connected to the light source device 11 and the processor device 12. Furthermore, if the calibration is performed, the correction coefficients $K_1$ and $K_2$ stored in the information storage 30 of the complementary color type endoscope 13a are preferably deleted and replaced with the correction coefficients $K_1$ and $K_2$ newly calculated by the mixed color corrector 48.

The mixed color correction processing according to the expression (3) lowers a mixed color component (a green narrowband light Gn component in the first mixed pixel signal M1 and a violet narrowband light Vn component in the second mixed pixel signal M2). The first and second mixed pixel signals M1' and M2' after the mixed color correction are sent to the channel allocator 38.

The primary color first processor 43 is chosen in a case where the endoscope 13 is of the primary color type and the observation mode is the normal light observation mode. To the primary color first processor 43, the RGB signal is inputted from the primary color type imaging device 29. In this RGB signal, one of R, G, and B signals is assigned to each pixel. The primary color first processor 43 produces three signals of R, G, and B for each pixel by performing well-known pixel interpolation processing. The RGB signals produced by the pixel interpolation processing are sent to the channel allocator 38.

The primary color second processor 44 is chosen in a case where the endoscope 13 is of the primary color type and the observation mode is the narrowband light observation mode. To the primary color second processor 44, the RGB signal is inputted from the primary color type imaging device 29. The primary color second processor 44 extracts a B signal for sensing the violet narrowband light Vn and a G signal for sensing the green narrowband light Gn, and produces a B signal and a G signal of each pixel by applying the pixel interpolation processing as with above. The B signal and the G signal are sent to the channel allocator 38.

In the normal light observation mode, the channel allocator 38 receives the RGB signals irrespective of the type of the endoscope 13, and hence allocates the R, G, and B signals to an R channel, a G channel, and a B channel of the image display device 14, respectively. Therefore, the normal image, that is, an image of the observation object irradiated with the normal light is displayed on the image display device 14.

In a case where the endoscope 13 is of the complementary color type and the narrowband light observation mode is chosen, the channel allocator 38 assigns the first and second mixed pixel signals M1' and M2' inputted from the complementary color second processor 42 to the channels of the image display device 14 as indicated by the following expression (4):

$$\begin{pmatrix} Rch \\ Gch \\ Bch \end{pmatrix} = \begin{pmatrix} 0 & 1 \\ 1 & 0 \\ 1 & 0 \end{pmatrix} \begin{pmatrix} M1' \\ M2' \end{pmatrix} \quad (4)$$

Therefore, an image of the observation object irradiated with the violet narrowband light Vn and the green narrowband light Gn is displayed as the special image on the image display device 14. Since the expression (4) assigns the first mixed pixel signal M1' corresponding to the violet narrowband light Vn to the two channels, the special image is such an image in which the structure of the superficial blood vessels (blood capillary) and the like in the vicinity of the surface of a living body is easily visible. Note that, the first and second mixed pixel signals M1' and M2' may be weighted by coefficients other than "0" or "1" in assignment to the channels.

Furthermore, provided that the endoscope 13 is of the primary color type and the narrowband light observation mode is chosen, the channel allocator 38 assigns the B signal and the G signal inputted from the primary color second processor 44 to the channels of the image display device 14 as indicated by the following expression (5):

$$\begin{pmatrix} Rch \\ Gch \\ Bch \end{pmatrix} = \begin{pmatrix} 0 & 1 \\ 1 & 0 \\ 1 & 0 \end{pmatrix} \begin{pmatrix} B \\ G \end{pmatrix} \quad (5)$$

Thus, an image of the observation object irradiated with the violet narrowband light Vn and the green narrowband light Gn is displayed as the special image on the image display device 14. This special image is such an image in which the structure of the superficial blood vessels and the like in the vicinity of the surface of the living body is easily visible. In a like manner, the B signal and the G signal may be weighted by coefficients other than "0" or "1" in assignment to the channels.

Next, a method for obtaining the expression (1), which determines the confines of the light amount ratio Z, will be described. The first and second mixed pixel signals M1 and M2 are represented by the following expression (6), wherein "X" and "Y" represent the light amounts of the violet narrowband light Vn and the green narrowband light Gn, respectively, simultaneously applied from the complementary color type endoscope 13a to the observation object, and "$a_1$" represents average sensitivity of the first mixed pixels (Mg+Cy) to the violet narrowband light Vn, and "$b_1$" represents average sensitivity of the first mixed pixels (Mg+Cy) to the green narrowband light Gn, and "$a_2$" represents average sensitivity of the second mixed pixels (G+Ye) to the green narrowband light Gn, and "$b_2$" represents average sensitivity of the second mixed pixels (G+Ye) to the violet narrowband light Vn. The average sensitivity refers to an average of sensitivity in the wavelength band of each type of narrowband light.

$$\begin{pmatrix} M1 \\ M2 \end{pmatrix} = \begin{pmatrix} a_1 & b_1 \\ b_2 & a_2 \end{pmatrix} \begin{pmatrix} X \\ Y \end{pmatrix} \quad (6)$$

Using the sensitivity $a_1$, $b_1$, $a_2$, $b_2$, the correction coefficients $K_1$ and $K_2$ used in the above mixed color correction processing are represented by the following expressions (7) and (8).

$$K_1 = \frac{M2v}{M1v} = \frac{b_2}{a_1} \quad (7)$$

$$K_2 = \frac{M1g}{M2g} = \frac{b_1}{a_2} \quad (8)$$

By applying the mixed color correction represented by the expression (3) to the first and second mixed pixel signals M1 and M2 represented by the expression (6), first and second mixed pixel signals M1' and M2' after the mixed color correction are represented by the following expressions (9) and (10).

$$M1' = \left(a_1 - \frac{b_1 b_2}{a_2}\right) X = (1 - K_1 K_2) a_1 X \quad (9)$$

$$M2' = \left(a_2 - \frac{b_1 b_2}{a_1}\right) Y = (1 - K_1 K_2) a_2 Y \quad (10)$$

Thus, the following expression (11) represents a condition of the light amount ratio Z (=X/Y) that makes the light amount X of the violet narrowband light Vn higher than the light amount Y of the green narrowband light Gn applied simultaneously to the observation object (X>Y), and makes the signal value M2' of the second mixed pixel used for imaging the green narrowband light Gn higher than the signal value M1' used for imaging the violet narrowband light Vn (M1'<M2').

$$1 < Z < \frac{a_2}{a_1} \quad (11)$$

The first mixed pixel signal M1v obtained in independent application of only the violet narrowband light Vn of the light amount $X_i$ is represented by the following expression (12). The second mixed pixel signal M2g obtained in independent application of only the green narrowband light Gn of the light amount $Y_i$ is represented by the following expression (13):

$$M1v = a_1 X_i \quad (12)$$

$$M2g = a_2 Y_i \quad (13)$$

Substituting the expressions (12) and (13) into the expression (11) brings the above expression (1). Referring to FIG. 12, $a_1 \approx 0.45$ and $a_2 \approx 0.98$, so these values are substituted into the expression (11). Thus, the light amount ratio Z defined by the expression (1) is in the confines of 1<Z<2.2, and the optimal light amount ratio $Z_0$ is approximately 1.6.

Figure 16:
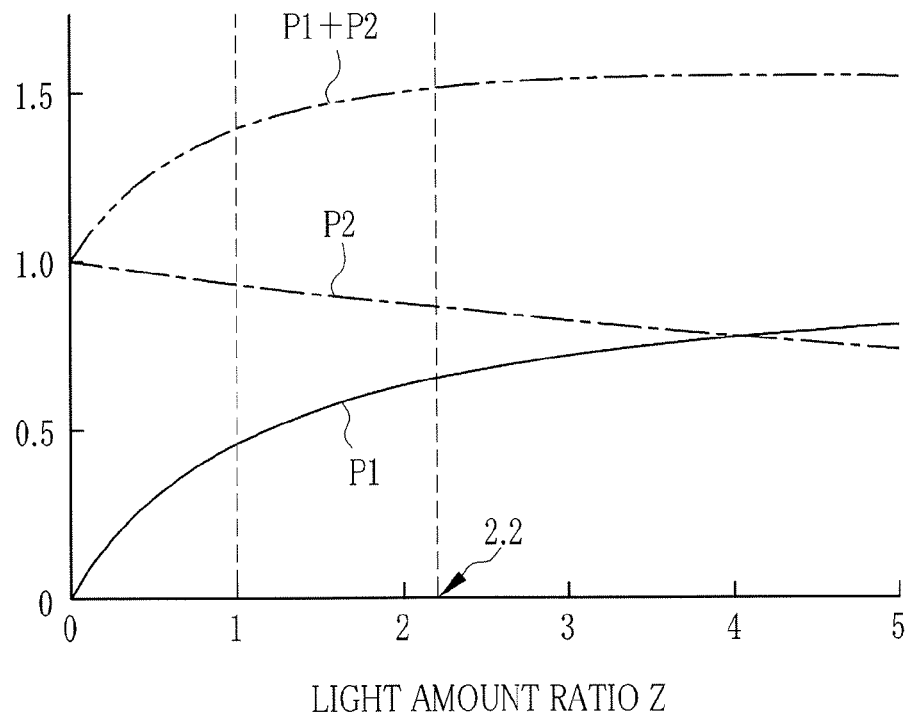
FIG. 16 is a graph showing the rate of a main component of each of first and second mixed pixel signals and the sum of the rates.

FIG. 16 shows a ratio P1 (=$a_1 X/(a_1 X + b_1 Y)$) of the violet narrowband light Vn component in the first mixed pixel signal M1, a ratio P2 (=$a_2 Y/(a_2 Y + b_2 X)$) of the green narrowband light Gn component in the second mixed pixel signal M2, and the sum (P1+P2) of the ratios P1 and P2, with respect to the light amount ratio Z (=X/Y). Wherein, $a_1 \approx 0.45$, $a_2 \approx 0.98$, $b_1 \approx 0.53$, and $b_2 \approx 0.07$ based on the spectral sensitivity characteristics of FIG. 12.

In the confines of the light amount ratio Z of 1<Z<2.2, the ratio P1 increases while the ratio P2 decreases, relative to a value at Z=1. However, an increase rate of the ratio P1 is larger than a decrease rate of the ratio P2, so the sum of the ratios P1 and P2 increases (i.e. an S/N ratio increases). Therefore, in this confines, the color separability between the violet narrowband light Vn component and the green narrowband light Gn component is improved, and the signal value M2' of the second mixed pixel used for imaging the green narrowband light Gn is increased more than the signal value M1' of the first mixed pixel used for imaging the violet narrowband light Vn. The green narrowband light Gn is easily reflected by the mucosa membrane and the like, though most of the violet narrowband light Vn is absorbed by hemoglobin in the superficial blood vessels. Therefore, M2'>M1' translates into increase in the light amount of the reflected light from the mucosa membrane and the like, and hence improvement in the visibility of the superficial blood vessels (the contrast between the superficial blood vessels and the mucosa membrane).

Figure 17:
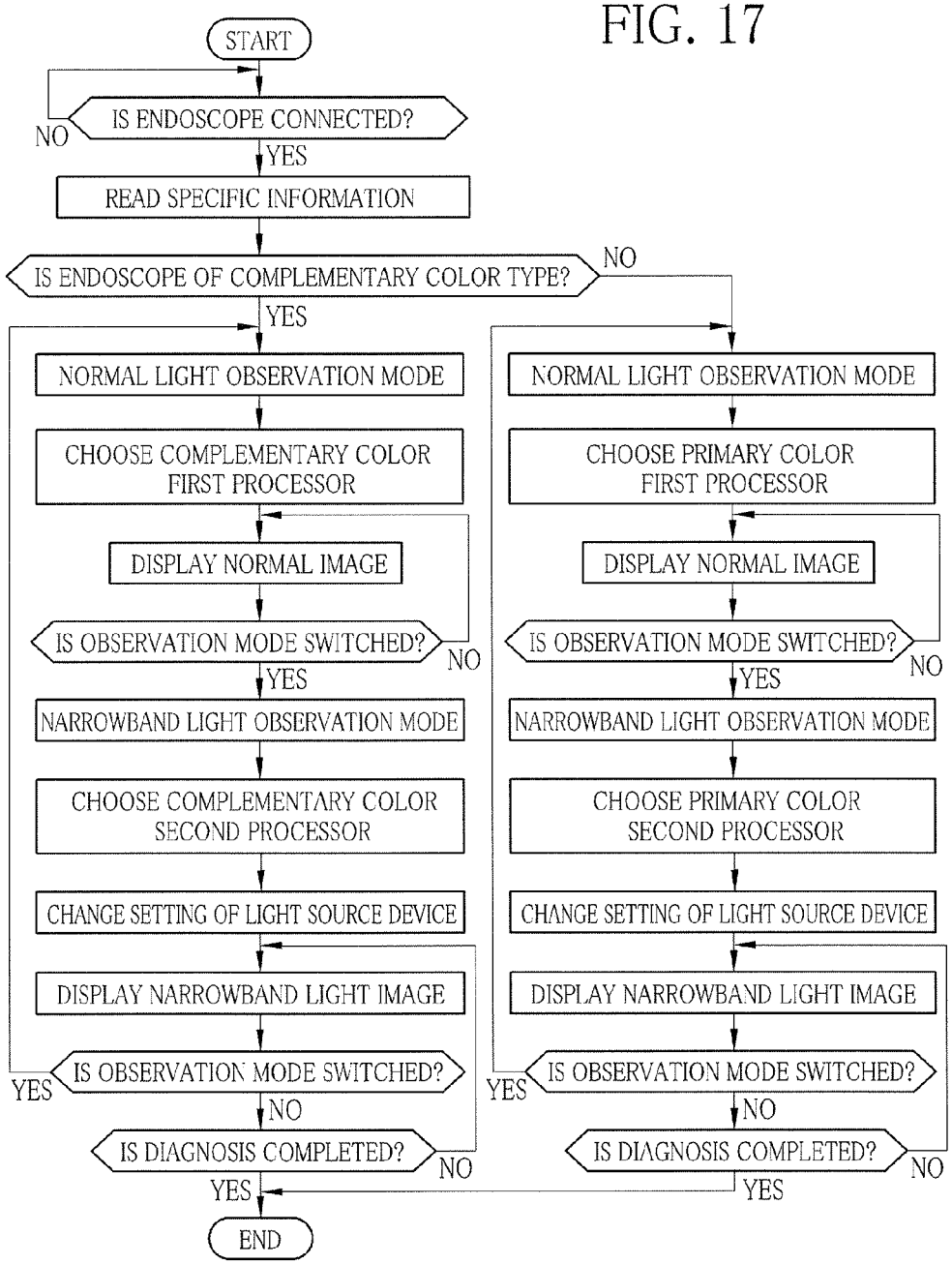
FIG. 17 is a flowchart of the operation of the endoscope system.

Next, the operation of the endoscope system 10 will be described with referring to a flowchart of FIG. 17. Upon connecting the endoscope 13 to the light source device 11 and the processor device 12, the main controller 31 of the processor device 12 reads the specific information from the information storage 30 of the endoscope 13 to judge whether the connected endoscope is the complementary color type endoscope 13a or the primary color type endoscope 13b. For example, in the case of the complementary color type endoscope 13a, the main controller 31 puts the light source device 11 and the processor device 12 into the normal light observation mode, and makes the selector 40 select the complementary color first processor 41 in the signal processing unit 37.

In the normal light observation mode, the dichroic mirror 22 is retracted to a position illustrated by a dotted line in FIG. 5 in the optical combiner 24 of the light source device 11, and the WL-LED 20b is turned on. The normal light (white light) WL from the WL-LED 20b is supplied to the light guide 27 of the complementary color type endoscope 13a. Also, the complementary color type imaging device 28 of the complementary color type endoscope 13a is driven by the imaging controller 32 by the field readout method, and outputs the first to fourth mixed pixel signals M1 to M4. The first to fourth mixed pixel signals M1 to M4 are subjected to the Y/C processing and converted into the RGB signal in the complementary color first processor 41, and displayed on the image display device 14 through the channel allocator 38. Thus, the normal image captured under the normal light is displayed on the image display device 14.

The insert section 16 of the complementary color type endoscope 13a is introduced into a patient's body cavity to perform endoscopy. To inspect the pattern of the superficial blood vessels and the like in tissue to be inspected such as a lesion inside the body cavity, the mode switch 17a is operated. The main controller 31 detects the operation signal of the mode switch 17a, and the light source device 11 and the processor device 12 are put into the narrowband light observation mode.

In the narrowband light observation mode, the selector 40 selects the complementary color second processor 42 and the setting of the light source device 11 is changed. To be more specific, the dichroic mirror 22 is disposed at the intersection point of the optical axes of the V-LED 20a and the WL-LED 20b in the optical combiner 24. At this time, the main controller 31 controls the light source device 21 based on the optimal light amount ratio $Z_0$ contained in the specific information read out of the information storage 30 so as to change the intensity ratio between the V-LED 20a and the WL-LED 20b, such that the violet narrowband light Vn and the green narrowband light Gn exit from the complementary color type endoscope 13a at the light amount ratio Z satisfying the above expression (1).

The V-LED 20a and the WL-LED 20b are simultaneously turned on, and the violet narrowband light Vn and the green narrowband light Gn are mixed in the optical combiner 24. The mixed narrowband light is supplied to the light guide 27 of the complementary color type endoscope 13a. The complementary color type imaging device 28 is driven by the field readout method, and outputs the first to fourth mixed pixel signals M1 to M4. In the complementary color second processor 42, the signal extractor 46 extracts the first and second mixed pixel signals M1 and M2 from the first to fourth mixed pixel signals M1 to M4. Then, the interpolator 47 applies the pixel interpolation processing to the first and second mixed pixel signals M1 and M2, and the mixed color corrector 48 applies the mixed color correction to the first and second mixed pixel signals M1 and M2 and outputs the corrected first and second mixed pixel signals M1' and M2'. The channel allocator 38 assigns the second mixed pixel signal M2' to the R channel and assigns the first mixed pixel signal M1' to the G channel and the B channel, so the first and second mixed pixel signals M1' and the M2' are displayed on the image display device 14. Therefore, the special image captured under the narrowband light is displayed on the image display device 14.

Since the violet narrowband light Vn is transmittable from the surface of the observation object to a first transmission distance in the vicinity of a superficial layer, a first image, which is based on the violet narrowband light Vn, contains much of an image of structure at the first transmission distance, such as the superficial blood vessels. This first image is produced based on the first mixed pixel signal M1. On the other hand, since the green narrowband light Gn is transmittable from the surface of the observation object to a second transmission distance in the vicinity of a middle to deep layer, a second image, which is based on the green narrowband light Gn, contains much of an image of structure at the second transmission distance, such as middle to deep blood vessels. The second image has high visibility of a minute pattern and the like of the mucosa membrane. This second image is produced based on the second mixed pixel signal M2. The first image and the second image are combined into the special image.

According to this embodiment, the light amount ratio Z is set based on the optimal light amount ratio $Z_0$ so as to satisfy the expression (1) (preferably, set at $Z=Z_0$). Therefore, it is possible to obtain the special image that has improved color separability and improved visibility of the superficial blood vessels (improved contrast between the superficial blood vessels and the mucosa membrane).

The special image is repeatedly displayed until the mode switch 17a is operated or completion operation for completing the endoscopy is performed from the input device 15. Upon operating the mode switch 17a, the endoscope system 10 is put back into the normal observation mode. The completion operation ends the operation.

On the other hand, in a case where the main controller 31 judges that the primary color type endoscope 13b is connected to the light source device 11 and the processor device 12, the light source device 11 and the processor device 12 are put into the normal light observation mode, and the selector 40 selects the primary color first processor 43. In the normal light observation mode, as in the case of the complementary color type, the normal light (white light) WL is produced by the light source device 11 and supplied to the light guide 27 of the primary color type endoscope 13b.

In this case, the primary color type imaging device 29 is driven by the progressive readout method and outputs the RGB signal. This RGB signal is subjected to the pixel interpolation processing and the like in the primary color first processor 43, and displayed on the image display device 14 through the channel allocator 38. Thus, the normal image captured under the normal light is displayed on the image display device 14.

After that, upon operating the mode switch 17a, the light source device 11 and the processor device 12 are put into the narrowband light observation mode. In the narrowband light observation mode, the selector 40 selects the primary color second processor 44, and the setting of the light source device 11 is changed so that the dichroic mirror 22 is disposed at the intersection point of the optical axes of the V-LED 20a and the WL-LED 20b in the optical combiner 24. In this case, in contrast to the complementary color type, the light emission intensity ratio between the V-LED 20a and the WL-LED 20b is set so as to satisfy $Z=1$. The narrowband light, being the mixture of the violet narrowband light Vn and the green narrowband light Gn, is produced and supplied to the light guide 27 of the primary color type endoscope 13b.

The primary color type imaging device 29 is driven by the progressive readout method and outputs the RGB signal. Out of the RGB signal, the primary color second processor 44 extracts only the B signal and the G signal. The B signal and the G signal are subjected to the pixel interpolation processing and the like, and displayed on the image display device 14 through the channel allocator 38. Thus, the special image captured under the narrowband light is displayed on the image display device 14.

As in the case of the complementary color type, the special image is displayed repeatedly until the mode switch 17a is operated or the completion operation is performed from the input device 15. Upon operating the mode switch 17a, the endoscope system 10 is put back into the normal observation mode. The completion operation ends the operation.

In a case where the complementary color type endoscope 13a is connected to the light source device 11 and the processor device 12, the calibration for recalculating the optimal light amount ratio $Z_0$ can be performed by operation of the input device 15 or the like. In the calibration, a white plate or the like is used as an object to be imaged.

In the calibration, the selector 40 selects the calibration processor 45, and the violet narrowband light Vn and the green narrowband light Gn are applied at the currently used light amount ratio Z in a time sharing manner. The complementary color type imaging device 28 outputs the first mixed pixel signals M1v and M1g and the second mixed pixel signals M2g and M2v, and the calibration processor 45 calculates an average of each signal value. Then, the optimal light amount ratio calculator 39 calculates the optimal light amount ratio $Z_0$ based on the currently used light amount ratio Z and the average value of each of the first and second mixed pixel signals M1v and M2g. The main controller 31 sets the calculated optimal light amount ratio $Z_0$ to the light source device 11, and deletes and replaces the optimal light amount ratio $Z_0$ stored in the information storage 30 of the complementary color endoscope 13a.

The first mixed pixel signals M1v and M1g and the second mixed pixel signals M2g and M2v obtained in the calibration are used for calculating the correction coefficients $K_1$ and $K_2$. The calculated correction coefficients $K_1$ and $K_2$ are written to the information storage 30 of the complementary color type endoscope 13a and used in the next use of the complementary color type endoscope 13a.

Note that, the light amount ratio Z is set by regulating the light emission intensity of the V-LED 20a and the WL-LED 20b in the above embodiments, but may be set by regulating light emission time. Furthermore, both of the light emission intensity and the light emission time may be regulated in order to set the light amount ratio Z.

Figure 18:
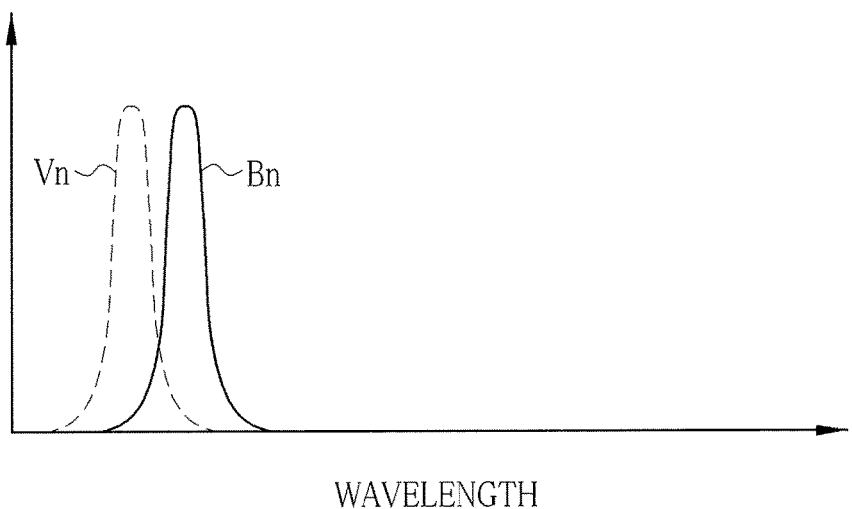
FIG. 18 is a graph showing an emission spectrum of blue narrowband light.

The LED light source 20 contains the V-LED 20a and the WL-LED 20b in the above embodiment, but a blue LED, which emits blue narrowband light Bn having a wavelength band on a longer side than the violet narrowband light Vn, as shown in FIG. 18, may be used instead of the V-LED 20a. The center wavelength of the blue narrowband light Bn is within the confines of approximately 410 nm to 420 nm, and preferably at approximately 415 nm.

Instead of the V-LED 20a and the WL-LED 20b, a plurality of LEDs (for example, four LEDs) having different emission wavelength bands may be provided. Turning on all the LEDs produces the normal light (white light), while turning on two of the LEDs produces two types of narrowband light. Furthermore, another type of semiconductor light source such as an LD (laser diode) may be used instead of the LED.

Figure 19:
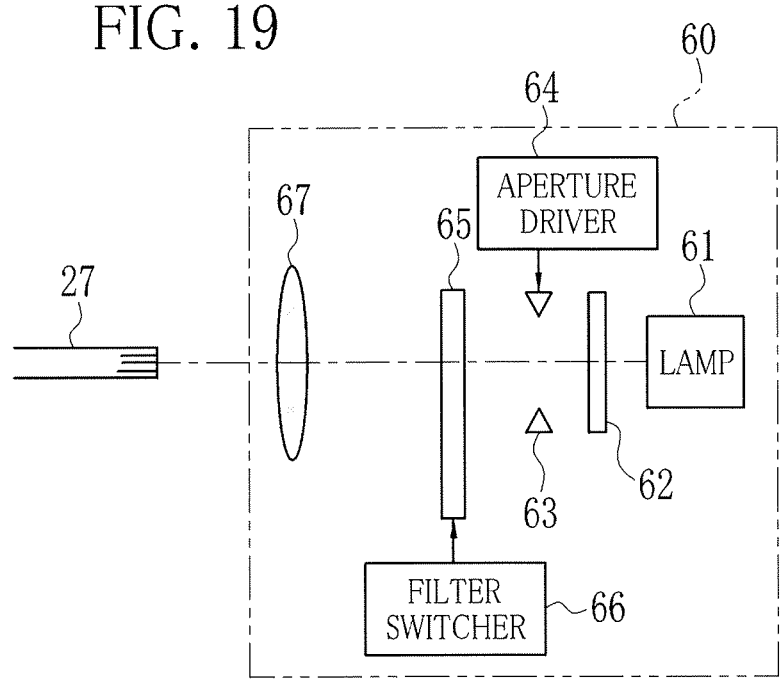
FIG. 19 is a schematic view of a modification example of a light source device.

Another light source device that has a lamp for emitting light having a wide wavelength band such as white light and a narrowband filter may be used instead of the light source device 11 described in the above embodiment. In FIG. 19, a light source device 60 includes a lamp 61, an infrared cut filter 62, an aperture stop 63, an aperture driver 64, a rotary filter unit 65, a filter switcher 66, and a condenser lens 67.

The lamp 61 emits white light WL under the control of the above main controller 31. The infrared cut filter 62 cuts an infrared component out of the white light WL produced by the lamp 61, so the remaining component enters the aperture stop 63. The aperture driver 64 regulates the opening size of the aperture stop 63 to adjust the transmission light amount of the white light WL. This aperture driver 64 is controlled by the dimmer 36 described above.

Figure 20:
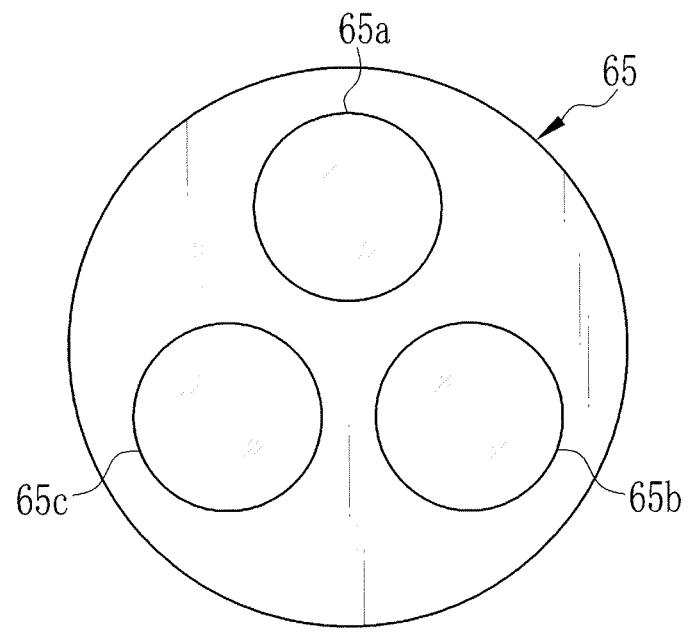
FIG. 20 is a schematic view of a rotary filter unit.

As shown in FIG. 20, the rotary filter unit 65 has a first narrowband filter 65a, a second narrowband filter 65b, and an opening 65c. The filter switcher 66 turns the rotary filter unit 65 under the control of the main controller 31, so that one of the first narrowband filter 65a, the second narrowband filter 65b, and the opening 65c is disposed in an optical axis of the white light WL.

Figure 21:
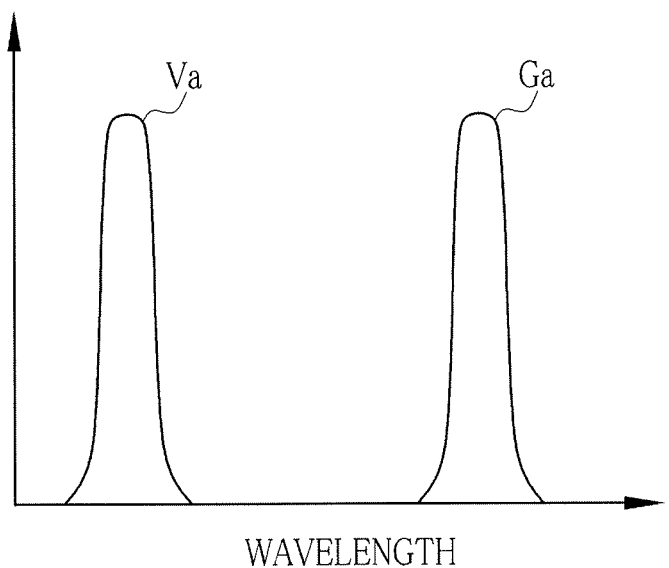
FIG. 21 is a graph showing a transmission characteristic of a first narrowband filter.

As shown in FIG. 21, the first narrowband filter 65a is a two-peak filter, which has a first characteristic section Va having a band-pass characteristic at a first narrowband (a center wavelength of 405 nm) and a second characteristic section Ga having a band-pass characteristic at a second narrowband (a center wavelength of 540 nm). The first characteristic section Va and the second characteristic section Ga have approximately equal transmittance.

This first narrowband filter 65a is disposed in the optical axis of the white light WL, in a case where the narrowband light observation mode is chosen and the endoscope 13 is of the primary color type. Passing the white light WL through the first narrowband filter 65a produces the violet narrowband light Vn and the green narrowband light Gn. The violet narrowband light Vn and the green narrowband light Gn enter the light guide 27 through the condenser lens 67. The light guide 27 has the spectral attenuation characteristic as shown in FIG. 13. The transmittance of the first characteristic section Va may be set a little higher than the transmittance of the second characteristic section Ga in consideration of the spectral attenuation characteristic and the like, so as to substantially equalize the light amounts of the violet narrowband light Vn and the green narrowband light Gn exiting from the light guide 27.

Figure 22:
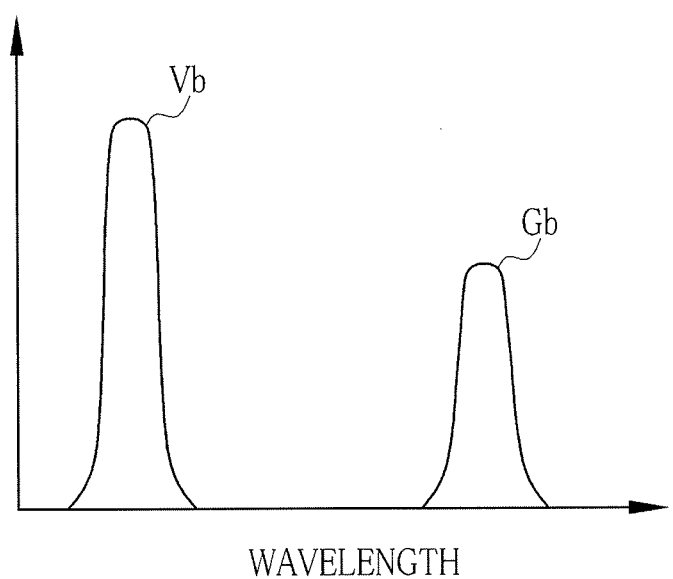
FIG. 22 is a graph showing a transmission characteristic of a second narrowband filter.

As shown in FIG. 22, the second narrowband filter 65b is a two-peak filter that has a first characteristic section Vb having a band-pass characteristic in a first narrowband and a second characteristic section Gb having a band-pass characteristic in a second narrowband. The first characteristic section Vb and the second characteristic section Gb have much different transmittance.

This second narrowband filter 65b is disposed in the optical axis of the white light WL, in a case where the narrowband light observation mode is chosen and the endoscope 13 is of the complementary color type. Passing the white light WL through the second narrowband filter 65b produces the violet narrowband light Vn and the green narrowband light Gn having a predetermined light amount ratio corresponding to the transmittance ratio between the first and second characteristic sections Vb and Gb. The violet narrowband light Vn and the green narrowband light Gn enter the light guide 27 through the condenser lens 67.

The transmittance ratio between the first and second characteristic sections Vb and Gb is set in consideration of the spectral attenuation characteristic of the light guide 27 and the like, such that the light amount ratio Z between the violet narrowband light Vn and the green narrowband light Gn exiting from the light guide 27 satisfies the expression (1) (preferably, $Z=Z_0$).

The opening 65c is disposed in the optical axis of the white light WL in a case where the normal observation mode is chosen. The opening 65c passes the white light WL incident thereon as-is without limiting its wavelength. The white light WL enters the light guide 27 through the condenser lens 67, and exits from the light guide 27 as the normal light.

Figure 23:
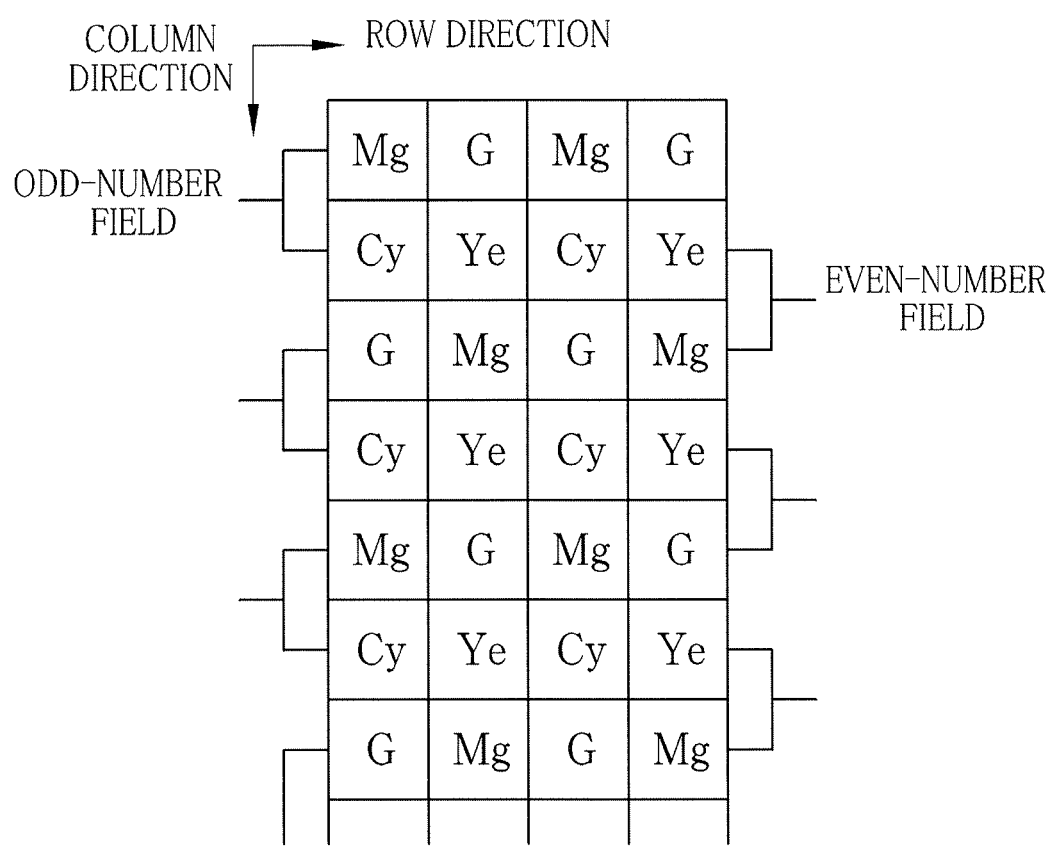
FIG. 23 is a schematic view of a modification example of the complementary color type color separation filter.

The above embodiments use the complementary color type imaging device 28 having the complementary color type color separation filter 28a of the complementary-color checkered-pattern color-difference line sequential method, as shown in FIG. 7, but may use another complementary color type imaging device having another complementary color type color separation filter, as shown in FIG. 23, of the complementary-color checkered-pattern color-difference line sequential method, instead.

In the above embodiments, the combination of the Mg pixel and the Cy pixel composes the first mixed pixel, and the combination of the G pixel and the Ye pixel composes the second mixed pixel. However, the combinations of mixed pixels are not limited to these and arbitrarily changeable.

According to the above embodiments, in the calibration mode, the violet narrowband light Vn and the green narrowband light Gn are applied at the currently used light amount ratio Z in a time-sharing manner, and the optimal light amount ratio $Z_0$ is calculated based on this light amount ratio Z and the signal values of the first and second mixed pixels. Instead of this, the violet narrowband light Vn and the green narrowband light Gn may be applied with stepwise change of the light amount ratio Z in a time-sharing manner, and the magnitude relation between the signal value M1' of the first mixed pixel and the signal value M2' of the second mixed pixel obtained at each light amount ratio Z may be judged, in order to determine the confines corresponding to the expression (1) and the optimal light amount ratio $Z_0$ corresponding to the expression (2).

According to the above embodiments, the imaging controller 32, the CDS circuit 33, the A/D converter 34, and the like are contained in the processor device 12, but may be provided in the endoscope 13.

In the above embodiments, the complementary color type imaging device 28 and the primary color type imaging device 29 are constituted of the CCD image sensors, but may be constituted of CMOS image sensors. In the case of the CMOS image sensor, the imaging controller 32, the CDS circuit 33, the A/D converter 34, and the like are formable in a CMOS semiconductor substrate formed with the image sensor.

According to the above embodiments, both of the complementary color type endoscope and the primary color type endoscope are connectable to the light source device and the processor device, but only the complementary color type endoscope may be connectable thereto.

In the above embodiments, the light source device and the processor device are configured as independent devices, but may be formed into a single device. Furthermore, the light source device may be incorporated in the endoscope.

Note that, "lighting section" described in claims corresponds to a combination of "light source device" and "optical members (light guide, lighting lens, and the like) for leading light from the light source device and applying the light to an observation object" described in the embodiments.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope system comprising:
   a complementary color type endoscope including a complementary color type imaging device having pixels to each of which one of color filter segments of cyan, magenta, yellow and green is attached;
   a lighting section having a light source device for generating first narrowband light having a center wavelength in a blue or violet wavelength range and second narrowband light having a center wavelength in a green wavelength range, said complementary color type endoscope being detachably connected to said light source device; and
   a controller for setting a first light amount ratio at a value more than 1, said first light amount ratio being a light amount ratio of a light amount of said first narrowband light to a light amount of said second narrowband light in case of said complementary color type endoscope being connected to said light source device,
   wherein said complementary color type endoscope and a primary color type endoscope having a primary color type imaging device are detachably connected to said light source device, and
   wherein said controller sets said first light amount ratio at a value more than a value of a second light amount ratio, said second light amount ratio being a light amount ratio of a light amount of said first narrowband light to a light amount of said second narrowband light in case of said primary color type endoscope being connected to said light source device.

2. The endoscope system according to claim 1, wherein said lighting section simultaneously applies said first narrowband light and said second narrowband light to an observation object.

3. The endoscope system according to claim 1, wherein
   a first mixed pixel and a second mixed pixel are read out from said complementary color type imaging device, each of said first mixed pixel and said second mixed pixel sensing both of said first narrowband light and said second narrowband light,
   said endoscope system further comprises a signal processing unit for imaging said first narrowband light by using a signal value of said first mixed pixel, and imaging said second narrowband light by using a signal value of said second mixed pixel, and
   said controller sets said first light amount ratio such that a signal value of said second mixed pixel is made higher than a signal value of said first mixed pixel.

4. The endoscope system according to claim 1, further comprising an image display device having an R channel, a G channel and a B channel, a signal corresponding to said first narrowband light being assigned to said G channel and said B channel.

5. The endoscope system according to claim 1, wherein said light source device includes a plurality of LED light sources, and said controller sets said first light amount ratio by regulating at least one of light emission intensity and light emission time of said plurality of LED light sources.

6. An endoscope system comprising:
a complementary color type endoscope including a complementary color type imaging device having pixels to each of which one of color filter segments of cyan, magenta, yellow and green is attached;
a lighting section having a light source device for generating first narrowband light having a center wavelength in a blue or violet wavelength range and second narrowband light having a center wavelength in a green wavelength range, said complementary color type endoscope being detachably connected to said light source device; and
a controller for setting a first light amount ratio at a value more than 1, said first light amount ratio being a light amount ratio of a light amount of said first narrowband light to a light amount of said second narrowband light in case of said complementary color type endoscope being connected to said light source device,
wherein a first mixed pixel and a second mixed pixel are read out from said complementary color type imaging device, said first mixed pixel being a combination of a magenta pixel and a cyan pixel, said second mixed pixel being a combination of a green pixel and a yellow pixel, each of said first mixed pixel and said second mixed pixel sensing both of said first narrowband light and said second narrowband light, and sensitivity of said second mixed pixel to said second narrowband light being higher than sensitivity of said first mixed pixel to said first narrowband light,
said endoscope system further comprises a signal processing unit for imaging said first narrowband light by using a signal value of said first mixed pixel, and imaging said second narrowband light by using a signal value of said second mixed pixel, and
said controller sets said first light amount ratio such that a signal value of said second mixed pixel is made higher than a signal value of said first mixed pixel.

* * * * *